(12) United States Patent
Nishina et al.

(10) Patent No.: US 8,330,110 B2
(45) Date of Patent: Dec. 11, 2012

(54) CONTAINER, CONTAINER POSITIONING METHOD, AND MEASURING METHOD

(75) Inventors: Shigeki Nishina, Miyagi (JP); Shigeaki Naitoh, Gunma (JP)

(73) Assignee: Advantest Corporation, Tokyo (JP)

( * ) Notice: Subject to any disclaimer, the term of this patent is extended or adjusted under 35 U.S.C. 154(b) by 499 days.

(21) Appl. No.: 12/617,129

(22) Filed: Nov. 12, 2009

(65) Prior Publication Data

US 2011/0057103 A1   Mar. 10, 2011

(30) Foreign Application Priority Data

Sep. 10, 2009 (JP) .................. 2009-209723

(51) Int. Cl.
  *G01J 5/02* (2006.01)
(52) U.S. Cl. ................. 250/341.1; 250/341.8
(58) Field of Classification Search ............. 250/341.1, 250/341.8
  See application file for complete search history.

(56) References Cited

U.S. PATENT DOCUMENTS

| | | | |
|---|---|---|---|
| 6,078,047 A | 6/2000 | Mittleman et al. | |
| 6,873,165 B2 * | 3/2005 | Lee et al. | 324/754.23 |
| 7,119,339 B2 | 10/2006 | Ferguson et al. | |
| 7,755,100 B2 * | 7/2010 | Choi et al. | 257/99 |
| 2007/0108382 A1 | 5/2007 | Itsuji | |
| 2007/0235658 A1 | 10/2007 | Zimdars et al. | |
| 2008/0252979 A1 | 10/2008 | Matsumoto | |
| 2010/0258727 A1 | 10/2010 | Itsuji et al. | |

FOREIGN PATENT DOCUMENTS

| | | |
|---|---|---|
| JP | 11-108845 | 4/1999 |
| JP | 2003-337201 | 11/2003 |
| JP | 2007-071585 | 3/2007 |
| JP | 2007-163170 | 6/2007 |
| JP | 2007-163181 | 6/2007 |
| JP | 2008-500541 | 1/2008 |
| JP | 2009-175127 | 8/2009 |
| WO | 2005/119214 | 12/2005 |
| WO | 2007/077658 | 7/2007 |

OTHER PUBLICATIONS

S. Wang et al., "Pulsed terahertz tomography", Journal of Physics D: Applied Physics, vol. 37 (2004) R1-R36.

* cited by examiner

*Primary Examiner* — Christine Sung
(74) *Attorney, Agent, or Firm* — Greenblum & Bernstein, P.L.C.

(57) ABSTRACT

A container according to the present invention contains at least a part of a device under test to be measured by a terahertz wave measurement device. The container includes a gap portion that internally disposes at least a part of the device under test, and an enclosure portion that includes a first flat surface portion and a second flat surface portion, and disposes the gap portion between the first flat surface portion and the second flat surface portion, thereby enclosing the gap portion. Moreover, a relationship $n1-0.1 \leq n2 \leq n1+0.1$ holds where $n2$ is a refractive index of the enclosure portion, and $n1$ is a refractive index of the device under test. Further, the first flat surface portion intersects with a travel direction of the terahertz wave at the right angle.

55 Claims, 23 Drawing Sheets

(a)

(b)

(c)

CONTAINER, CONTAINER POSITIONING METHOD, AND MEASURING METHOD

BACKGROUND ART

1. Field of the Invention

The present invention relates to tomography using an electromagnetic wave (frequency thereof is equal to or more than 0.01 [THz], and equal to or less than 100 [THz]) (such as a terahertz wave (frequency thereof is equal to or more than 0.03 [THz], and equal to or less than 10 [THz]), for example).

2. Description of the Prior Art

There has conventionally been the computed tomography (CT) as a method for obtaining tomographic information on a device under test. This method conducted while a generator and a detector of the X ray are used is referred to as X-ray CT. With the X-ray CT, it is possible to acquire tomographic information on a human body in non-destructive and non-contact manner.

However, it is difficult for the X-ray CT to detect internal states (such as defects and distortions) of industrial products constructed by semiconductors, plastics, ceramics, woods, and papers (referred to as "raw materials" hereinafter). This is because the X-ray presents a high transmission property to any materials.

On the other hand, the terahertz wave properly transmits through the raw materials of the industrial products described above. Therefore, the CT carried out while a generator and a detector of the terahertz wave (referred to as "terahertz CT" hereinafter) are used can detect internal states of the industrial products. Patent Document 1 and Non-Patent Document 1 describe the terahertz CT.

(Patent Document 1) U.S. Pat. No. 7,119,339
(Non-Patent Document 1) S. Wang et al., "Pulsed terahertz tomography," J. Phys. D, Vol. 37 (2004), R1-R36

SUMMARY OF THE INVENTION

However, according to the terahertz CT, when the terahertz wave is obliquely made incident to or emitted from a device under test, the terahertz wave is refracted, and thus does not travel straight. On this occasion, it is assumed that the refractive index of the ambient air of the device under test is 1, and the refractive index of the device under test for the terahertz CT is more than 1.

FIG. 23 shows estimated optical paths of the terahertz wave when the refractive index of a conventional device under test is 1.4, and the refractive index of the ambient air of the device under test is 1. Referring to FIG. 23, it is appreciated that terahertz wave made incident from the left of the device under test (DUT) are refracted by the DUT.

Due to the fact that the terahertz wave does not travel straight, the terahertz wave cannot reach a detector, and an image of the DUT cannot thus be obtained at a sufficient sensitivity.

Moreover, due to the fact that the terahertz wave does not travel straight, a detected terahertz wave may not have traveled straight through the DUT before the arrival. Therefore, when an image of the DUT is obtained from the detected terahertz wave, artifacts such as obstructive shadows and pseudo images may appear on the image.

Therefore, it is an object of the present invention, when an electromagnetic wave (frequency thereof is equal to or more than 0.01 [THz] and equal to or less than 100 [THz]) including the terahertz wave is supplied to a DUT for measurement, to restrain refraction of the electromagnetic wave including the terahertz wave by the DUT.

According to the present invention, a first container that contains at least a part of a device under test to be measured by an electromagnetic wave measurement device, includes: a gap portion that internally disposes at least a part of the device under test; and an enclosure portion that includes a first flat surface portion and a second flat surface portion, and disposes the gap portion between the first flat surface portion and the second flat surface portion, thereby enclosing the gap portion, wherein: n2 can be adjusted such that: $n1-0.1 \leq n2 \leq n1+0.1$ where n2 denotes a refractive index of the enclosure portion and n1 denotes a refractive index of the device under test; and the electromagnetic wave measurement device outputs an electromagnetic wave having a frequency equal to or more than 0.01 [THz] and equal to or less than 100 [THz] toward the device under test.

According to the thus constructed first container that contains at least a part of a device under test to be measured by an electromagnetic wave measurement device, a gap portion internally disposes at least a part of the device under test. An enclosure portion includes a first flat surface portion and a second flat surface portion, and disposes the gap portion between the first flat surface portion and the second flat surface portion, thereby enclosing the gap portion. n2 can be adjusted such that: $n1-0.1 \leq n2 \leq n1+0.1$ where n2 denotes a refractive index of the enclosure portion and n1 denotes a refractive index of the device under test. The electromagnetic wave measurement device outputs an electromagnetic wave having a frequency equal to or more than 0.01 [THz] and equal to or less than 100 [THz] toward the device under test.

According to the first container of the present invention, the refractive index of the enclosure portion may be changed by changing a thickness of the enclosure portion.

According to the first container of the present invention, the refractive index of the enclosure portion may be changed by compressing or extending the enclosure portion.

According to the first container of the present invention, the enclosure portion may be made of a foamable resin.

According to the first container of the present invention, the device under test may receive the electromagnetic wave while the device under test is rotated about a predetermined rotational axis; and the enclosure portion may be compressed or extended in a direction of the predetermined rotational axis.

According to the first container of the present invention, the device under test may receive the electromagnetic wave while the device under test is rotated about a predetermined rotational axis; and the enclosure portion may be compressed or extended in a direction orthogonal to the predetermined rotational axis, and to an optical path of the electromagnetic wave.

According to the first container of the present invention, the device under test may receive the electromagnetic wave while the container and an optical path of the electromagnetic wave are rotated about a predetermined rotational axis; and the enclosure portion may be compressed or extended in the direction of the predetermined rotational axis.

According to the first container of the present invention, the device under test may receive the electromagnetic wave while the container and an optical path of the electromagnetic wave are rotated about a predetermined rotational axis; and the enclosure portion may be compressed or extended in a direction orthogonal to the predetermined rotational axis, and to the optical path of the electromagnetic wave.

According to the first container of the present invention, the enclosure portion may be compressed or extended in a direction parallel with an optical path of the electromagnetic wave.

According to the first container of the present invention, a contour of a plane shape of the gap portion may include an arc.

According to the first container of the present invention, a radius of the contour of the plane shape of the gap portion may change according to the height of the gap portion.

According to the first container of the present invention, the enclosure portion can be separated along a separation surface; and the separation surface may intersect with the gap portion.

According to the present invention, a refractive index adjustment method for adjusting the refractive index of the enclosure portion of the first container of the present invention containing the device under test, includes: a step of arranging the container such that the first flat surface portion intersects with a travel direction of the electromagnetic wave output from the electromagnetic wave measurement device toward the device under test at the right angle; and a step of adjusting the refractive index of the enclosure portion such that an optical path of the electromagnetic wave incident to the first flat surface portion and an optical path of the electromagnetic wave which has transmitted through the enclosure portion and the device under test are aligned on a straight line.

According to the present invention, a container arrangement method for arranging the first container of the present invention containing the device under test for measuring the device under test by the electromagnetic wave measurement device, includes a step of arranging the container such that the first flat surface portion intersects with a travel direction of the electromagnetic wave output from the electromagnetic wave measurement device toward the device under test at the right angle.

According to the present invention, a container arrangement method for arranging the first container of the present invention containing the device under test for measuring the device under test by the electromagnetic wave measurement device, includes a step of arranging the container such that the first flat surface portion intersects with a travel direction of the electromagnetic wave output from the electromagnetic wave measurement device toward the device under test at an angle more than 0 degree and less than 90 degrees.

According to the present invention, a second container that contains at least a part of a device under test to be measured by an electromagnetic wave measurement device, includes a plurality of first structures that includes: a first gap portion which internally disposes at least a part of the device under test, and a first enclosure portion which includes a first flat surface portion and a second flat surface portion, and disposes the first gap portion between the first flat surface portion and the second flat surface portion, thereby enclosing the first gap portion, wherein: the first structures are separated by a predetermined interval; n2 can be adjusted such that: $n1-0.1 \leq n2 \leq n1+0.1$ where n2 denotes a average refractive index of the container and n1 denotes a refractive index of the device under test; and the electromagnetic wave measurement device outputs an electromagnetic wave having a frequency equal to or more than 0.01 [THz] and equal to or less than 100 [THz] toward the device under test.

According to the thus constructed second container that contains at least a part of a device under test to be measured by an electromagnetic wave measurement device, a plurality of first structures includes: a first gap portion and a first enclosure portion. The first gap portion internally disposes at least a part of the device under test. The first enclosure portion includes a first flat surface portion and a second flat surface portion, and disposes the first gap portion between the first flat surface portion and the second flat surface portion, thereby enclosing the first gap portion. The first structures are separated by a predetermined interval. n2 can be adjusted such that: $n1-0.1 \leq n2 \leq n1+0.1$ where n2 denotes a average refractive index of the container and n1 denotes a refractive index of the device under test. The electromagnetic wave measurement device outputs an electromagnetic wave having a frequency equal to or more than 0.01 [THz] and equal to or less than 100 [THz] toward the device under test.

According to the second container of the present invention, the average refractive index of the container may be Changed by changing the predetermined interval.

According to the second container of the present invention, the predetermined interval may be changed by compressing or extending the container.

The second container of the present invention may include an interval retaining member that is provided between a plurality of the first structures, and is provided outside the first gap portion.

The second container of the present invention may include a second structure provided between a plurality of the first structures, wherein the second structure includes: a second gap portion which internally disposes at least a part of the device under test; and a second enclosure portion which includes a third flat surface portion and a fourth flat surface portion, and disposes the second gap portion between the third flat surface portion and the fourth flat surface portion, thereby enclosing the second gap portion.

According to the second container of the present invention, the predetermined interval may be determined so as not to cause a Bragg reflection of the electromagnetic wave.

According to the second container of the present invention, the predetermined intervals may be equal to each other.

According to the second container of the present invention, the predetermined intervals may include an unequal interval.

According to the second container of the present invention, the device under test may receive the electromagnetic wave while rotating about a predetermined rotational axis; and the container may be compressed or extended in the direction of the predetermined rotational axis.

According to the second container of the present invention, the device under test may receive the electromagnetic wave while the container and an optical path of the electromagnetic wave are rotated about a predetermined rotational axis; and the container may be compressed or extended in the direction of the predetermined rotational axis.

According to the second container of the present invention, a contour of a plane shape of the first gap portion may include an arc.

According to the second container of the present invention, a radius of the contour of the plane shape of the first gap portion may change according to the height of the first gap portion.

According to the second container of the present invention, the first enclosure portion can be separated along a separation surface; and the separation surface may intersect with the first gap portion.

According to the present invention, a refractive index adjustment method for adjusting the average refractive index of the second container of the present invention containing the device under test, includes: a step of arranging the container so that a normal direction of the first flat surface portion is parallel with a travel direction of the electromagnetic wave output from the electromagnetic wave measurement device toward the device under test; and a step of adjusting the average refractive index of the container such that an optical path of the electromagnetic wave incident to the first flat surface portion and an optical path of the electromagnetic wave which has transmitted through the container and the device under test are aligned on a straight line.

According to the present invention, a container arrangement method for arranging the second container of the present invention containing the device under test for measuring the device under test by the electromagnetic wave measurement device, includes a step of arranging the container so that a normal direction of the first flat surface portion is parallel with a travel direction of the electromagnetic wave output from the electromagnetic wave measurement device toward the device under test.

According to the present invention, a container arrangement method for arranging the second container of the present invention containing the device under test for measuring the device under test by the electromagnetic wave measurement device, includes a step of arranging the container such that a normal direction of the first flat surface portion intersects with a travel direction of the electromagnetic wave output from the electromagnetic wave measurement device toward the device under test at an angle more than 0 degree and less than 90 degrees.

According to the present invention, a third container that contains at least a part of a device under test to be measured by an electromagnetic wave measurement device, includes a plurality of first structures that are separated by a predetermined interval in a predetermined direction, wherein n2 can be adjusted such that: $n1-0.1 \leq n2 \leq n1+0.1$ where n2 denotes a average refractive index of the container and n1 denotes a refractive index of the device under test; the electromagnetic wave measurement device outputs an electromagnetic wave having a frequency equal to or more than 0.01 [THz] and equal to or less than 100 [THz] toward the device under test; a through gap portion which passes through the container internally disposes at least a part of the device under test; and an extending direction of the through gap portion and the predetermined direction intersects with each other at the right angle.

According to the thus constructed third container that contains at least a part of a device under test to be measured by an electromagnetic wave measurement device, a plurality of first structures are separated by a predetermined interval in a predetermined direction. n2 can be adjusted such that: $n1-0.1 \leq n2 \leq n1+0.1$ where n2 denotes a average refractive index of the container and n1 denotes a refractive index of the device under test. The electromagnetic wave measurement device outputs an electromagnetic wave having a frequency equal to or more than 0.01 [THz] and equal to or less than 100 [THz] toward the device under test. A through gap portion which passes through the container internally disposes at least a part of the device under test. An extending direction of the through gap portion and the predetermined direction intersects with each other at the right angle.

According to the third container of the present invention, the average refractive index of the container can be changed by changing the predetermined interval.

According to the third container of the present invention, the predetermined interval may be changed by compressing or extending the container.

The third container of the present invention may include an interval retaining member that is provided between a plurality of the first structures.

The third container of the present invention may includes a second structure provided between a plurality of the first structures.

According to the third container of the present invention, the predetermined interval may be determined so as not to cause a Bragg reflection of the electromagnetic wave.

According to the third container of the present invention, the predetermined intervals may be equal to each other.

According to the third container of the present invention, the predetermined intervals may include an unequal interval.

According to the third container of the present invention, the device under test may receive the electromagnetic wave while the device under test is rotated about a predetermined rotational axis; and the container may be compressed or extended in a direction orthogonal to the predetermined rotational axis, and to an optical path of the electromagnetic wave.

According to the third container of the present invention, the device under test may receive the electromagnetic wave while the container and an optical path of the electromagnetic wave are rotated about a predetermined rotational axis; and the container may be compressed or extended in a direction orthogonal to the predetermined rotational axis, and to an optical path of the electromagnetic wave.

The third container of the present invention may be compressed or extended in a direction parallel with an optical path of the electromagnetic wave.

According to the third container of the present invention, a contour of a plane shape of the through gap portion may include an arc.

According to the third container of the present invention, a radius of the contour of the plane shape of the through gap portion may change according to the height of the through gap portion.

According to the third container of the present invention, the container can be separated along a separation surface; and the separation surface intersects with the through gap portion.

According to the present invention, a refractive index adjustment method for adjusting the average refractive index of the third container of the present invention containing the device under test, includes: a step of arranging the container so that the predetermined direction is parallel with or orthogonal to a travel direction of the electromagnetic wave output from the electromagnetic wave measurement device toward the device under test; and a step of adjusting the average refractive index of the container such that an optical path of the electromagnetic wave incident to the container and an optical path of the electromagnetic wave which has transmitted through the container and the device under test are aligned on a straight line.

According to the present invention, a container arrangement method for arranging the third container of the present invention containing the device under test for measuring the device under test by the electromagnetic wave measurement device, includes a step of arranging the container such that the predetermined direction is parallel with or orthogonal to a travel direction of the electromagnetic wave output from the electromagnetic wave measurement device toward the device under test.

According to the present invention, a container arrangement method for arranging the third container of the present invention containing the device under test for measuring the device under test by the electromagnetic wave measurement device, includes a step of arranging the container such that the predetermined direction intersects with a travel direction of the electromagnetic wave output from the electromagnetic wave measurement device toward the device under test at an angle more than 0 degree and less than 90 degrees.

According to the present invention, a method for measuring the device under test contained in the container according to the present invention using the electromagnetic wave measurement device, includes: an output step of outputting the electromagnetic wave by the electromagnetic wave measurement device; and a detection step of detecting the electromagnetic wave which has transmitted through the device under test by the electromagnetic wave measurement device, wherein the container and the device under test move horizontally with respect to an optical path of the electromagnetic wave while the output step and the detection step are being carried out.

According to the present invention, a method for measuring the device under test contained in the container according to the present invention using the electromagnetic wave measurement device, includes: an output step of outputting the electromagnetic wave by the electromagnetic wave measurement device; and a detection step of detecting the electromagnetic wave which has transmitted through the device under test by the electromagnetic wave measurement device, wherein an optical path of the electromagnetic wave move horizontally with respect to the container while the output step and the detection step are being carried out.

According to the present invention, a method for measuring the device under test contained in the container according to the present invention using the electromagnetic wave measurement device, includes: an output step of outputting the electromagnetic wave by the electromagnetic wave measurement device; and a detection step of detecting the electromagnetic wave which has transmitted through the device under test by the electromagnetic wave measurement device, wherein the device under test is rotated about a line extending vertically as a rotational axis while the output step and the detection step are being carried out.

According to the present invention, a method for measuring the device under test contained in the container according to the present invention using the electromagnetic wave measurement device, includes: an output step of outputting the electromagnetic wave by the electromagnetic wave measurement device; and a detection step of detecting the electromagnetic wave which has transmitted through the device under test by the electromagnetic wave measurement device, wherein the container and an optical path of the electromagnetic wave are rotated about a line extending vertically as a rotational axis while the output step and the detection step are being carried out.

According to the present invention, a method for measuring the device under test contained in the container according to the present invention using the electromagnetic wave measurement device, includes: an output step of outputting the electromagnetic wave by the electromagnetic wave measurement device; and a detection step of detecting the electromagnetic wave which has transmitted through the device under test by the electromagnetic wave measurement device, wherein the container and an optical path of the electromagnetic wave move vertically with respect to the device under test while the output step and the detection step are being carried out.

According to the present invention, a method for measuring the device under test contained in the container according to the present invention using the electromagnetic wave measurement device, includes: an output step of outputting the electromagnetic wave by the electromagnetic wave measurement device; and a detection step of detecting the electromagnetic wave which has transmitted through the device under test by the electromagnetic wave measurement device, wherein the container and the device under test move vertically with respect to an optical path of the electromagnetic wave while the output step and the detection step are being carried out.

According to the present invention, a method for measuring the device under test contained in the container according to the present invention using the electromagnetic wave measurement device, includes: an output step of outputting the electromagnetic wave by the electromagnetic wave measurement device; and a detection step of detecting the electromagnetic wave which has transmitted through the device under test by the electromagnetic wave measurement device, wherein the device under test moves vertically with respect to the container and an optical path of the electromagnetic wave while the output step and the detection step are being carried out.

According to the present invention, a method for measuring the device under test contained in the container according to the present invention using the electromagnetic wave measurement device, includes: an output step of outputting the electromagnetic wave by the electromagnetic wave measurement device; and a detection step of detecting the electromagnetic wave which has transmitted through the device under test by the electromagnetic wave measurement device, wherein an optical path of the electromagnetic wave moves vertically with respect to the container and the device under test while the output step and the detection step are being carried out.

BRIEF DESCRIPTION OF THE DRAWINGS

FIGS. 2(a) to 2(c) are views of the container 10 when the enclosure portion 12 is clamped by the upper pressing member 16a and the lower pressing member 16b according to the first embodiment, in which FIG. 2(a) is a plan view; FIG. 2(b) is a b-b cross sectional view of FIG. 2(a); and FIG. 2(c) is a c-c cross sectional view of FIG. 2(a);

FIGS. 7(a), 7(b), and 7(c) are views of the container 10 according to the second embodiment, in which FIG. 7(a) is a plan view, FIG. 7(b) is a front view, and FIG. 7(c) is a plan view without the uppermost first structure 100, the bolt head portions 14a, and the bolt thread portions 14c;

FIGS. 9(a), 9(b), and 9(c) are views of the container 10 according to the third embodiment, in which FIG. 9(a) is a plan view, FIG. 9(b) is a front view, and FIG. 9(c) is a plan view without the upper pressing member 16a, the bolt head portions 14a, and the bolt thread portions 14c;

FIGS. 18(a) and 18(b) are views when the DUT 1 is stored in the container 10 according to the eleventh embodiment, in which FIG. 18(a) is a cross sectional view, and FIG. 18(b) is a plan view;

FIGS. 20(a) and 20(b) are views of a state in which at least a part of the DUT 1 is stored in the container 10 according to the second embodiment, and the terahertz wave is irradiated on the container 10, in which FIG. 20(a) is a plan view and FIG. 20(b) is a partial front view;

FIGS. 22(a) and 22(b) are views of a state in which at least a part of the DUT 1 is stored in the container 10 according to the third embodiment, and the terahertz wave is irradiated on the container 10, in which FIG. 22(a) is a plan view and FIG. 22(b) is a partial front view.

BEST MODE FOR CARRYING OUT THE INVENTION

A description will now be given of embodiments of the present invention with reference to drawings.

First Embodiment

Figure 1:
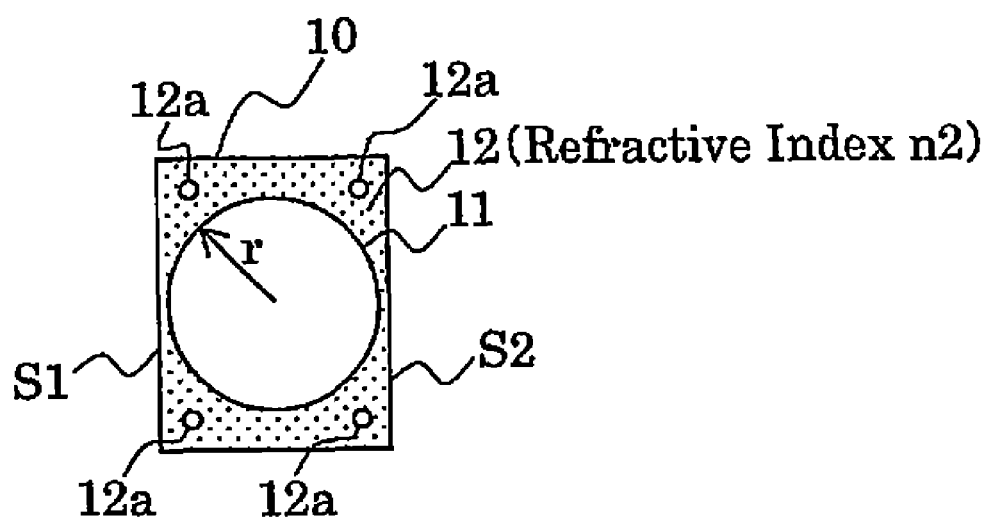
FIG. 1 is a plan view of a container 10 according to a first embodiment of the present invention.
Figure 4:
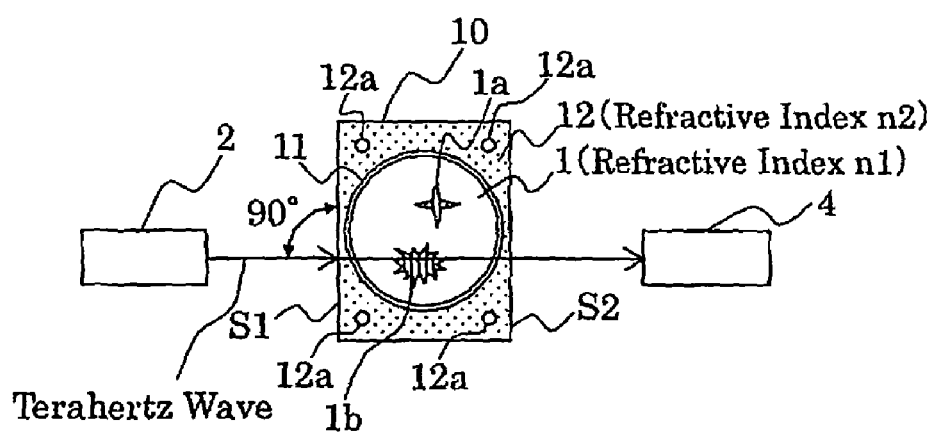
FIG. 4 is a plan view of a state in which at least a part of a device under test (DUT) 1 is stored in the container 10 according to the first embodiment of the present invention, and a terahertz wave is irradiated on the container 10.

FIG. 1 is a plan view of a container 10 according to a first embodiment of the present invention. FIG. 4 is a plan view of a state in which at least a part of a device under test (DUT) 1 is stored in the container 10 according to the first embodiment of the present invention, and a terahertz wave is irradiated on the container 10.

It should be noted that bolt head portions 14a, bolt thread portions 14c, and an upper pressing member 16a, which will be described later, are not shown in FIG. 4.

Referring to FIG. 4, a terahertz wave measurement device (electromagnetic wave measurement device) includes a terahertz wave output device 2 and a terahertz wave detector 4. The terahertz wave output device 2 outputs the terahertz wave. The terahertz wave detector 4 detects the terahertz wave which has transmitted through the DUT 1 and the container 10.

It should be noted that the terahertz wave measurement device (electromagnetic wave measurement device) employs, as an electromagnetic wave to be output and to be detected, the terahertz wave (the frequency thereof is equal to or more than 0.03 [THz] and equal to or less than 10 [THz], for example). However, the electromagnetic waves to be output and detected by the terahertz wave measurement device (electromagnetic wave measurement device) are not limited to the terahertz waves, and may be electromagnetic waves the frequency of which is equal to or more than 0.01 [THz] and equal to or less than 100 [THz].

The container 10 stores at least a part of the DUT 1 to be measured by the terahertz wave measurement device. It should be noted that the container 10 may store the DUT 1 partially (refer to FIGS. 14(a) and 14(b)) or entirely (refer to FIGS. 15(a) and 15(b)).

The container 10 includes a gap portion 11 and an enclosure portion 12. The gap portion 11 is a circular gap with a radius of r viewed from above (refer to FIG. 1). At least a part of the DUT 1 is disposed inside the gap portion 11 (refer to FIG. 4).

The enclosure portion 12 includes the first flat surface portion S1 and the second flat surface portion S2. It should be noted that the first flat surface portion S1 and the second flat surface portion S2 are represented by straight lines in FIGS. 1 and 4. This is because FIGS. 1 and 4 are plan views. Actually, the container 10 has a thickness (refer to FIGS. 14(a), 14(b), 15(a), and 15(b)), and the first flat surface portion S1 and the second flat surface portion S2 are thus not straight lines, but flat surfaces. It should be noted that the first flat surface portion S1 and the second flat surface portion S2 are parallel with each other.

It should be noted that a material of the enclosure portion 12 is a foamable resin (such as a urethane foam, a polyethylene foam, and a rubber foam). These foamable resins often have a refractive index equal to or less than 1.1.

Moreover, through holes 12a are provided at four corners of the enclosure portion 12. The bolt thread portion 14c passes through the enclosure portion 12 via the through hole 12a.

The gap portion 11 is arranged between the first flat surface portion S1 and the second flat surface portion S2. The enclosure portion 12 encloses the gap portion 11. On this occasion, a refractive index of the DUT 1 is denoted by n1, and a refractive index of the enclosure portion 12 is denoted by n2. Then, n2 can be adjusted so that a relationship $n1-0.1 \leq n2 \leq n1+0.1$ holds. It is preferable that a relationship $n1=n2$ holds. Moreover, n1 and n2 may not be equal to the refractive index (such as 1) of ambient air of the container 10.

The refractive index n2 of the enclosure portion 12 can be changed by changing the thickness of the enclosure portion 12. According to the first embodiment, the refractive index of the enclosure portion 12 is changed by compressing or extending the enclosure portion 12. Specifically, the refractive index of the enclosure portion 12 is changed by clamping the enclosure portion 12 using the upper pressing member 16a and a lower pressing member 16b.

Figure 2:
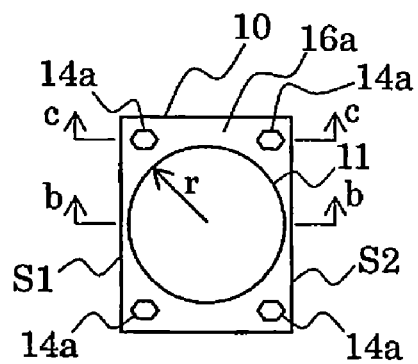
Figure 2:
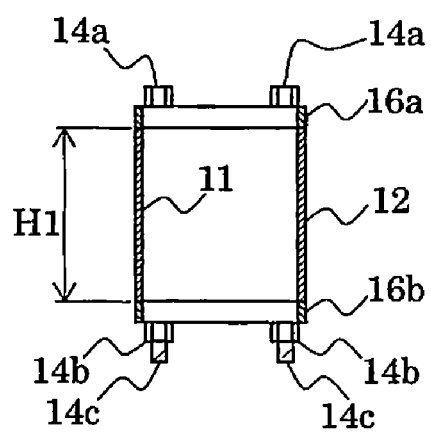
Figure 2:
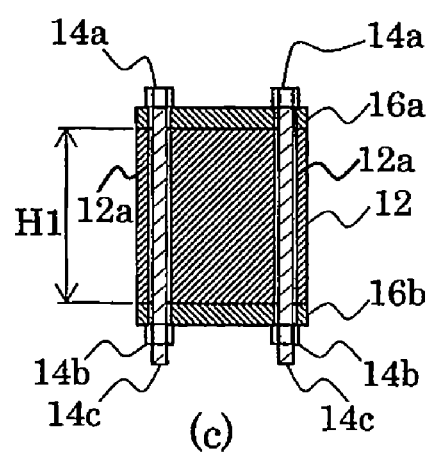

FIGS. 2(a) to 2(c) are views of the container 10 when the enclosure portion 12 is clamped by the upper pressing member 16a and the lower pressing member 16b according to the first embodiment, in which FIG. 2(a) is a plan view; FIG. 2(b) is a b-b cross sectional view of FIG. 2(a); and FIG. 2(c) is a c-c cross sectional view of FIG. 2(a).

A hole having the same diameter as that of the gap portion 11 is formed on the upper pressing member 16a and the lower pressing member 16b (refer to FIG. 2(b)), and the DUT 1 is placed inside thereof.

Referring to FIG. 2(c), the upper pressing member 16a is placed on a top of the enclosure portion 12. The lower pressing member 16b is placed on a bottom of the enclosure portion 12. The bolt head portion 14a is placed on a top of the upper pressing member 16a. The bolt thread portion 14c is integral with the bolt head portion 14a, and a male thread is provided thereupon. Moreover, a through hole continuing to the through hole 12a is formed in the upper pressing member 16a and the lower pressing member 16b. The bolt thread portion 14c passes through the through hole 12a (and through holes formed in the upper pressing member 16a and the lower pressing member 16b), thereby passing through the enclosure portion 12, the upper pressing member 16a, and the lower pressing member 16b. Nuts 14b are provided on a bottom surface of the lower pressing member 16b. The bolt thread portion 14c is threaded into the nut 14b.

On this occasion, the enclosure portion 12 can be compressed by turning the bolt head portions 14a to tighten the threads (of the bolt thread portions 14c) while the nuts 14b are fixed so as not to turn. It should be noted that the enclosure portion 12 can be extended by loosening the threads (of the bolt thread portions 14c).

A refractive index n2 in the state shown in FIG. 2(c) (height of the enclosure portion 12=H1) is represented by the following equation (1). It should be noted that H0 denotes a height of the enclosure portion 12 when the enclosure portion 12 is neither compressed nor extended. Moreover, n2o denotes a refractive index of the enclosure portion 12 when the enclosure portion 12 is neither compressed nor extended.

$$n2=1+(n2o-1)\times H0/H1 \quad (1)$$

It should be noted that the direction to compress or extend the enclosure portion 12 is a direction of the height of the enclosure portion 12 (Z direction, refer to FIGS. 14(a), 14(b), 15(a), and 15(b)).

Referring to FIG. 4, the first flat surface portion S1 intersects, at the right angle, with a travel direction of the terahertz wave output from the terahertz wave output device 2 of the terahertz wave measurement device toward the DUT 1. The container 10 is provided as described above to measure the DUT 1 by the terahertz wave measurement device.

A description will now be given of an operation of the first embodiment.

First, the refractive index n2 of the enclosure portion 12 is adjusted.

Figure 3:
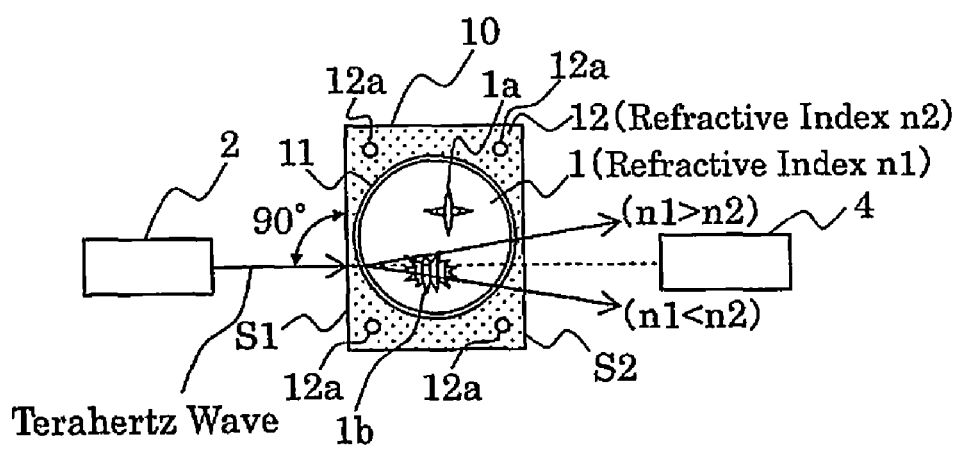
FIG. 3 illustrates the adjustment of the refractive index n2 of the enclosure portion 12 according to the first embodiment.

FIG. 3 illustrates the adjustment of the refractive index n2 of the enclosure portion 12 according to the first embodiment. It should be noted that the bolt head portions 14a and the upper pressing member 16a are not shown in FIG. 3.

First, at least a part of the DUT 1 is disposed inside the gap portion 11. Then, the container 10 is disposed such that the first flat surface portion S1 intersects, at the right angle, with the travel direction of the terahertz wave output from the terahertz wave output device 2 of the terahertz wave measurement device toward the DUT 1.

The terahertz wave output from the terahertz wave output device 2 is orthogonally irradiated on the first flat surface portion S1. As a result, the terahertz wave is not refracted, but travels straight, and proceeds inside the enclosure portion 12.

It should be noted that the thickness of an air layer between the contour of the DUT 1 and the contour of the plane shape of the gap portion 11 is thin, and is thus neglected.

On this occasion, when a relationship (refractive index n1 of DUT 1)>(refractive index n2 of enclosure portion 12) holds, the terahertz wave is refracted upward in FIG. 3 at an interface between the gap portion 11 and the DUT 1. It should be noted that an optical path on this occasion is shown in FIG. 3 while subsequent refractions are neglected.

Moreover, when a relationship (refractive index n1 of DUT 1)<(refractive index n2 of enclosure portion 12) holds, the terahertz wave is refracted downward in FIG. 3 at the interface between the gap portion 11 and the DUT 1. It should be noted that an optical path on this occasion is shown in FIG. 3 while subsequent refractions are neglected.

Therefore, unless a relationship (refractive index n1 of DUT 1)=(refractive index n2 of enclosure portion 12) holds, the terahertz wave will not continue to travel straight as described above.

On this occasion, when the relationship (refractive index n1 of DUT 1)>(refractive index n2 of enclosure portion 12) holds, the refractive index n2 of the enclosure portion 12 is increased. For example, the enclosure portion 12 is compressed by turning the bolt head portions 14a to tighten the threads.

Moreover, when the relationship (refractive index n1 of DUT 1)<(refractive index n2 of enclosure portion 12) holds, the refractive index n2 of the enclosure portion 12 is decreased. For example, the enclosure portion 12 is extended by turning the bolt head portions 14a to loosen the threads.

As a result of the adjustment of the refractive index n2 of the enclosure portion 12 in this way, the relationship (refractive index n1 of DUT 1)=(refractive index n2 of enclosure portion 12) finally holds. Then, the terahertz wave transmits through the enclosure portion 12 and the DUT 1 while traveling straight, and is then made incident to the terahertz wave detector 4. In this case, the optical path of the terahertz wave incident to the first flat surface portion S1, and the optical path of the terahertz wave after the transmission through the enclosure portion 12 and the DUT 1 are aligned on a straight line. The refractive index of the enclosure portion 12 is adjusted as described above so as to provide this state.

The DUT 1 is then measured.

Referring to FIG. 4, the terahertz wave output device 2 of the terahertz wave measurement device outputs the terahertz wave. The terahertz wave output from the terahertz wave output device 2 is orthogonally irradiated on the first flat surface portion S1. As a result, the terahertz wave is not refracted, but travels straight, and proceeds inside the enclosure portion 12.

On this occasion, the thickness of the air layer between the contour of the DUT 1 and the contour of the plane shape of the gap portion 11 is thin, and is thus neglected. Further, it is assumed that the refractive index n2 of the enclosure portion 12 has already been adjusted such that the relationship (refractive index n1 of DUT 1)=(refractive index n2 of enclosure portion 12) holds.

Then, the terahertz wave, which has traveled inside the enclosure portion 12, is not refracted, but travels straight inside the DUT 1. Then, the terahertz wave transmits through the DUT 1, and is made incident to the enclosure portion 12. Further, the terahertz wave travels straight inside the enclosure portion 12, and transmits through the second flat surface portion S2. Finally, the terahertz wave output from the terahertz wave output device 2 transmits through the enclosure portion 12 and the DUT 1 while continuing to travel straight, and is made incident to the terahertz wave detector 4.

The terahertz wave detector 4 detects the incident terahertz wave. As a result, the DUT 1 is measured. For example, the DUT 1 includes contents 1a and 1b. Referring to FIG. 4, the terahertz wave transmits through the content 1b, and thus, the position and the like of the content 1b are revealed according to a result of the detection of the terahertz wave.

Though the operation of the first embodiment is described while assuming that the relationship (refractive index n1 of DUT 1)=(refractive index n2 of enclosure portion 12) holds, it can be considered that the terahertz wave output from the terahertz wave output device 2 transmits through the enclosure portion 12 and the DUT 1 while continuing to travel straight as long as the relationship $n1-0.1 \leq n2 \leq n1+0.1$ holds. Therefore, the refractive index n2 of the enclosure portion 12 may be adjusted so that the relationship n1−0.1≦n2≦n1+0.1 holds.

According to the first embodiment, it is possible to restrain the terahertz wave from being refracted by the DUT 1 when the DUT 1 is measured by supplying the DUT 1 with the terahertz wave.

It should be noted that various variations of the container 10 according to the first embodiment are conceivable.

Figure 5:
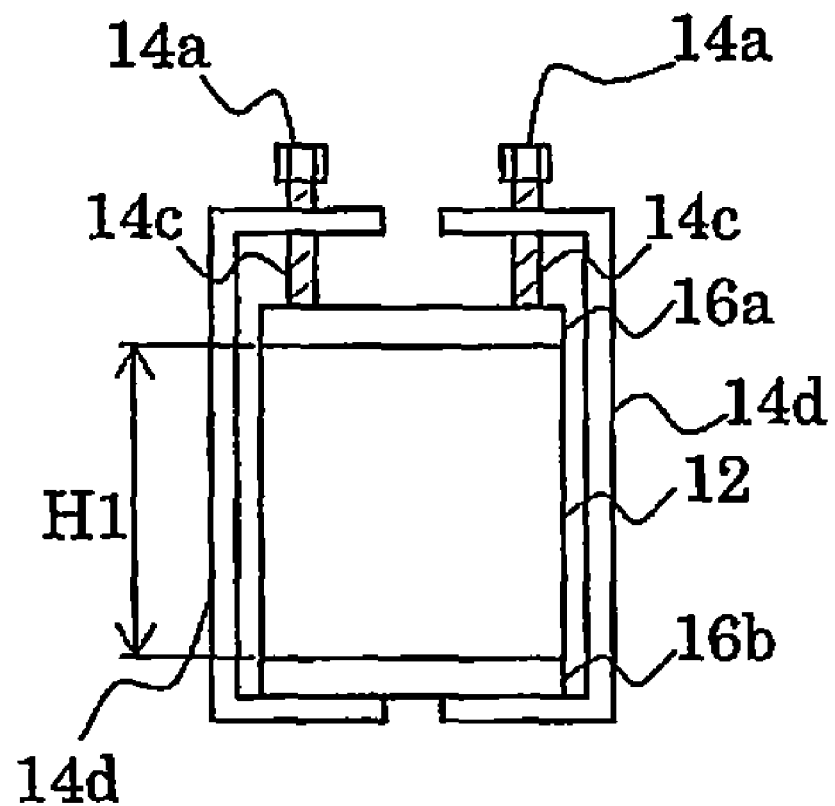
FIG. 5 is a front view of the container 10 showing a variation of the mechanism to compress or extend the enclosure portion 12.

FIG. 5 is a front view of the container 10 showing a variation of the mechanism to compress or extend the enclosure portion 12. Frames 14d are in close contact with the bottom surface of the lower pressing member 16b. Moreover, the bolt thread portions 14c passes through an upper portion of the frames 14d. It should be noted that a female thread is formed on the frame 14d, and matches the male thread of the bolt thread portion 14c. It should be noted that the bolt thread portions 14c do not pass through the upper pressing member 16a, and are in contact with a top surface of the upper pressing member 16a.

As a result, it is possible, by turning the bolt head portions 14a, thereby tightening the threads (of the bolt thread portions 14c), to cause the bolt thread portions 14c to press the upper pressing member 16a, thereby compressing the enclosure portion 12. Conversely, the enclosure portion 12 can be extended by loosening the threads (of the bolt thread portions 14c).

Figure 6:
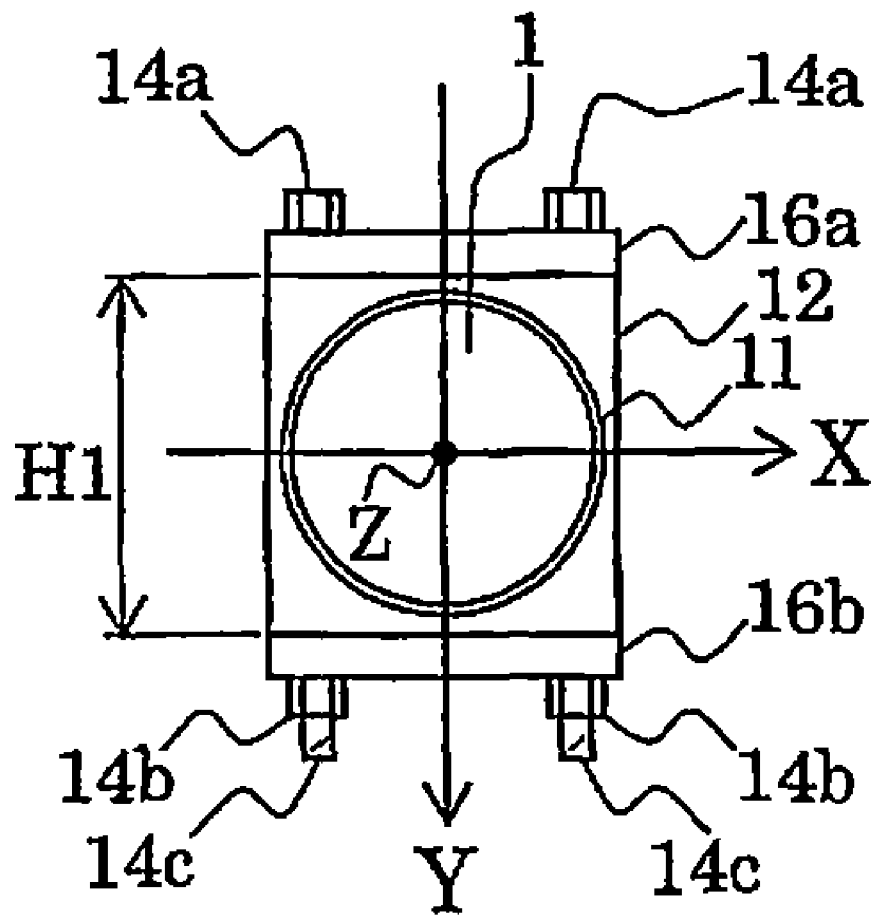
FIG. 6 is a plan view of the container 10 showing a variation in which the direction to compress or extend the enclosure portion 12 according to the first embodiment is changed.

FIG. 6 is a plan view of the container 10 showing a variation in which the direction to compress or extend the enclosure portion 12 according to the first embodiment is changed. Though the above-described direction in which the enclosure portion 12 is compressed or extended is the Z direction, the direction may be a Y direction (direction orthogonal to the Z direction). In this case, the direction in which the terahertz wave is made incident is the Y direction or an X direction.

When the direction in which the terahertz wave is made incident is the Y direction in the case shown in FIG. 6, the first flat surface portion S1 is a surface of the enclosure portion 12 in contact with the upper pressing member 16a, and the second flat surface portion S2 is a surface of the enclosure portion 12 in contact with the lower pressing member 16b.

Second Embodiment

The container 10 according to the second embodiment is different from the container 10 according to the first embodiment in that first structures 100 and spacers (interval maintaining members) 18 are provided in place of the enclosure portion 12 according to the first embodiment.

Figure 20:
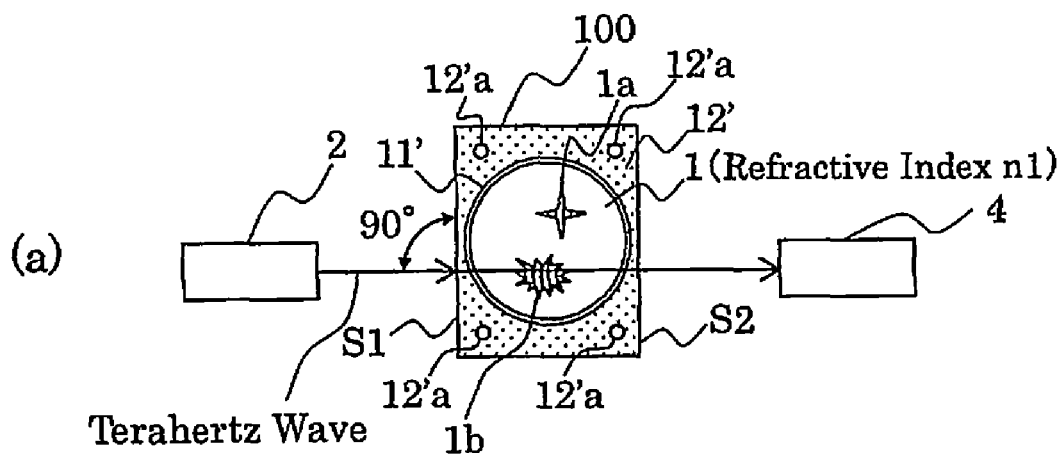
Figure 20:
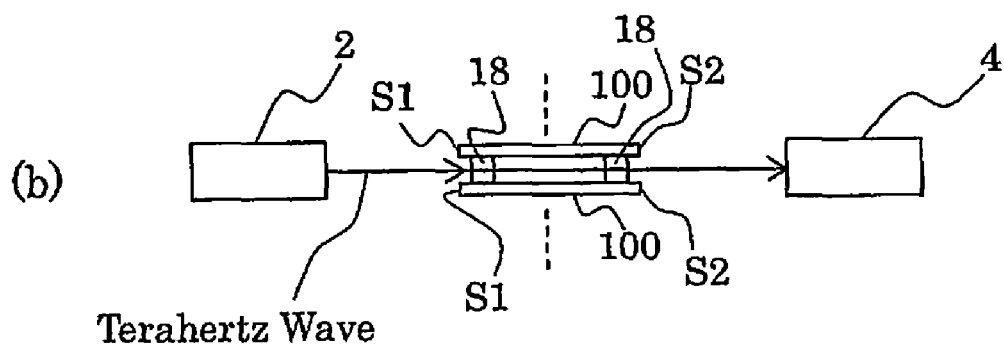

FIGS. 20(a) and 20(b) are views of a state in which at least a part of the DUT 1 is stored in the container 10 according to the second embodiment, and the terahertz wave is irradiated on the container 10, in which FIG. 20(a) is a plan view and FIG. 20(b) is a partial front view. It should be noted that the bolt head portions 14a and the bolt thread portions 14c are not shown in FIG. 20(a). FIG. 20(b) only shows a neighborhood of a position through which the terahertz wave transmits. It should be noted that FIG. 20(a) is approximately the same as FIG. 4 (when the enclosure portion 12 is replaced by the first structure 100). Moreover, the terahertz wave output device 2 and the terahertz wave detector 4 included in the terahertz wave measurement device (electromagnetic wave measurement device) are the same as those of the first embodiment. The frequency of the electromagnetic wave output and detected by the terahertz wave measurement device (electromagnetic wave measurement device) is the same as that of the first embodiment.

FIGS. 7(a), 7(b), and 7(c) are views of the container 10 according to the second embodiment, in which FIG. 7(a) is a plan view, FIG. 7(b) is a front view, and FIG. 7(c) is a plan view without the uppermost first structure 100, the bolt head portions 14a, and the bolt thread portions 14c. The container 10 according to the second embodiment is provided with the first structures 100 and the spacers (interval maintaining members) 18.

The multiple first structures 100 are provided (six in the example shown in FIG. 7(b), but it is only necessary to provide two or more of them), and are separated by a predetermined interval H3. Moreover, the thickness of the first structures 100 is H2.

A first gap portion 11' and a first enclosure portion 12' included in the first structure 100 are the same as the gap portion 11 and the enclosure portion 12 according to the first embodiment (refer to FIG. 1), and the description thereof, therefore, is omitted. It should be noted that a material of the first structure 100 is a resin (refractive index is approximately 1.5) such as Teflon (registered trademark) or a ceramic plate (refractive index is approximately 2).

The spacers (interval maintaining members) 18 are disposed between the multiple first structures 100. The spacer 18 has elasticity.

On this occasion, a refractive index of the DUT 1 is denoted by n1, and an average refractive index of the container 10 is denoted by n2. Then, n2 can be adjusted so that a relationship n1−0.1≦n2≦n1+0.1 holds. It is preferable that the relationship n1=n2 holds. Moreover, n1 and n2 may not be equal to the refractive index (such as 1) of ambient air of the container 10.

The average refractive index n2 of the container 10 can be changed by changing the predetermined intervals H3. According to the second embodiment, the predetermined intervals H3 are changed by compressing or extending the container 10. Specifically, the average refractive index of the container 10 is changed by clamping the multiple first structures 100 using the bolt head portions 14a and the nuts 14b, thereby changing the predetermined intervals H3.

Referring to FIG. 7(b), the bolt head portions 14a are arranged on a top of the first structure 100 disposed at the top. The nuts 14b are arranged on a bottom of the lowest first structure 100. The bolt thread portion 14c is integrated with the bolt head portion 14a, and a male thread is provided thereupon. The bolt thread portion 14c passes through (through holes 12'a of) the first structures 100 (refer to FIGS. 19, 20(a), and 20(b)) and (through holes 18a of) the spacers 18 (refer to FIG. 7(c)). The bolt thread portion 14c is threaded into the nut 14b.

Referring to FIG. 7(c), the spacers 18 are arranged at four corners of the first structure 100, and it can be considered that an air is present between the first structures 100. Moreover, the spacers 18 are arranged outside the gap portion 11, and are dimensioned so as not to extend into the gap portion 11.

On this occasion, the predetermined intervals H3 can be reduced by turning the bolt head portions 14a to tighten the thread (of the bolt thread portions 14c) while the nuts 14b are fixed so as not to turn, thereby compressing the spacers 18 of the container 10. It should be noted that the predetermined intervals H3 can be increased by loosening the thread (of the bolt thread portions 14c), thereby extending the spacers 18 of the container 10.

Moreover, since it can be considered that the air is present between the first structures 100, the average refractive index n2 of the container 10 in the state shown in FIG. 7(b) is expressed by the following equation (2). It should be noted that n2' denotes a refractive index of the first structure 100.

Moreover, each of the predetermined intervals H3 are equal. In other words, it is assumed that the multiple first structures 100 are arranged at the equal interval.

$$n2=1+(n2'-1)\times H2/(H2+H3) \qquad (2)$$

It should be noted that the predetermined intervals H3 may be different from each other.

Moreover, the direction to compress or extend the container 10 is a direction of the height of the container 10 (Z direction, refer to FIGS. 14(a), 14(b), 15(a), and 15(b)).

Moreover, as in the first embodiment, referring to FIGS. 20(a) and 20(b), a direction of the normal line of the first flat surface portion S1 is parallel with the travel direction of the terahertz wave output from the terahertz wave output device 2 of the terahertz wave measurement device toward the DUT 1. The container 10 is provided as described above so as to measure the DUT 1 by the terahertz wave measurement device. The terahertz wave output toward the DUT 1 may be made incident to the first flat surface portion S1 of the first structure 100, or the space between the first structures 100 (refer to FIG. 20(b)).

When the terahertz wave output from the terahertz wave output device 2 is supplied to the container 10, a Bragg reflection may occur depending on the frequency of the terahertz wave. In this case, the terahertz wave hardly transmits through the container 10, and the Bragg reflection is thus preferably avoided.

The frequency $f_N$ (of the electromagnetic wave supplied to the container 10) which causes the Bragg reflection is represented by the following equation (3). It should be noted that N denotes an integer equal to or more than 1, and C denotes the velocity of light.

$$f_N = N \times C/(2 \times n2 \times (H2+H3)) \qquad (3)$$

On this occasion, the predetermined interval H3 is determined such that the frequency of the terahertz wave supplied to the container 10 is not close to the frequency $f_N$. In other words, the predetermined interval H3 is determined such that the terahertz wave does not present the Bragg reflection.

For example, a frequency $f_1$ is sufficiently higher than the frequency of the terahertz wave supplied to the container 10. Since a relationship $f_1 < f_2 < f_3 \ldots$ holds, the frequency of the terahertz wave supplied to the container 10 is lower than the frequency $f_N$. Moreover, the frequency of the terahertz wave supplied to the container 10 is set to approximately $1.5f_1$.

A description will now be given of an operation of the second embodiment.

First, the average refractive index n2 of the container 10 is adjusted.

Figure 19:
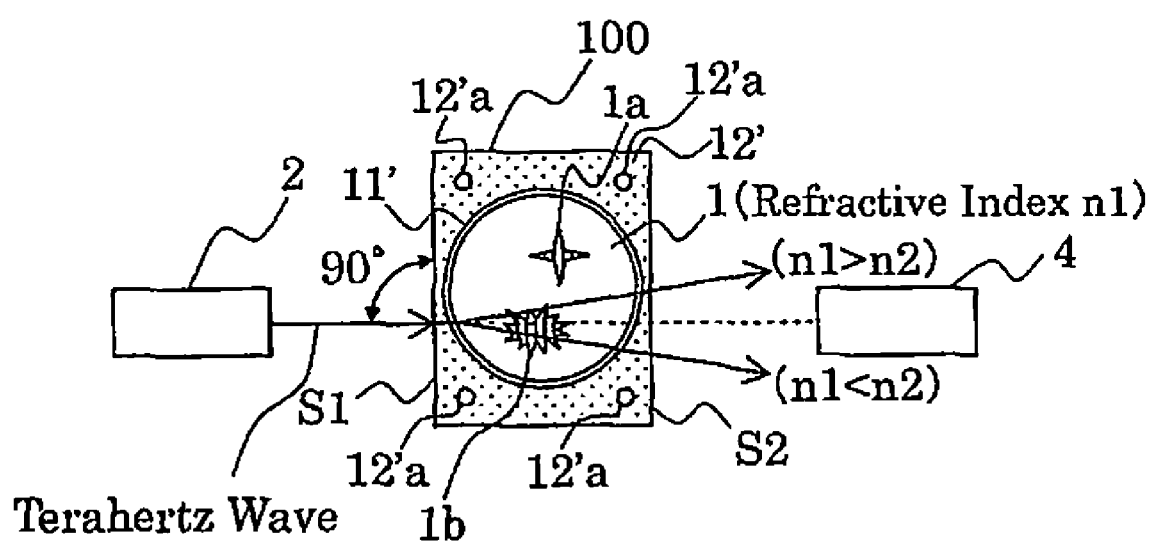
FIG. 19 illustrates the adjustment of the average refractive index n2 of the container 10 according to the second embodiment.

FIG. 19 illustrates the adjustment of the average refractive index n2 of the container 10 according to the second embodiment. It should be noted that the bolt head portions 14a and the bolt thread portions 14c are not shown in FIG. 19.

The average refractive index n2 of the container 10 is adjusted as in the first embodiment (refer to FIG. 3).

First, at least a part of the DUT 1 is disposed inside the gap portion 11. Then, the container 10 is disposed such that a direction of the normal line of the first flat surface portion S1 is parallel with the travel direction of the terahertz wave output from the terahertz wave output device 2 of the terahertz wave measurement device toward the DUT 1.

Unless a relationship (refractive index n1 of DUT 1)=(average refractive index n2 of container 10) holds, the terahertz wave is refracted at an interface between the gap portion 11 and the DUT 1, and will not continue to travel straight.

On this occasion, when the relationship (refractive index n1 of DUT 1)>(average refractive index n2 of container 10) holds, the refractive index n2 of the enclosure portion 12 is increased. For example, the container 10 is compressed by turning the bolt head portions 14a to tighten the threads.

Moreover, when the relationship (refractive index n1 of DUT 1)<(average refractive index n2 of container 10) holds, the refractive index n2 of the enclosure portion 12 is decreased. For example, the container 10 is extended by turning the bolt head portions 14a to loosen the threads.

As a result of the adjustment of the average refractive index n2 of the container 10 in this way, the relationship (refractive index n1 of DUT 1)=(average refractive index n2 of container 10) finally holds. Then, the terahertz wave transmits through the container 10 and the DUT 1 while traveling straight, and is then made incident to the terahertz wave detector 4. In this case, the optical path of the terahertz wave incident to the first flat surface portion S1, and the optical path of the terahertz wave after the transmission through the container 10 and the DUT 1 are aligned on a straight line. The refractive index of the container 10 is adjusted as described above so as to provide this state.

The DUT 1 is then measured.

Referring to FIGS. 20(a) and 20(b), the measurement of the DUT 1 is the same as that of the first embodiment (refer to FIG. 4).

According to the second embodiment, there are obtained the same effects as in the first embodiment.

It should be noted that the container 10 can be compressed or extended using the frames 14d as shown in FIG. 5 in the container 10 according to the second embodiment.

Figure 8:
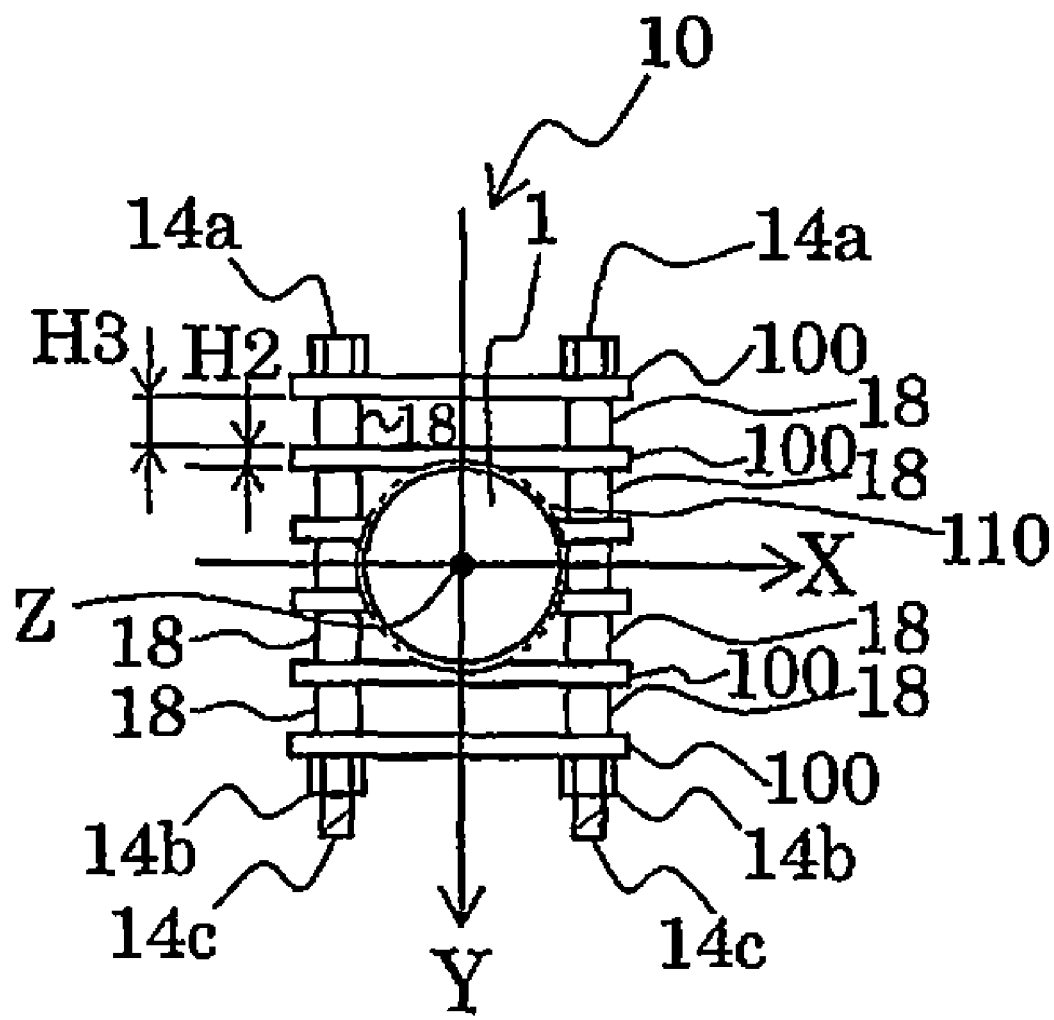
FIG. 8 is a plan view of the container 10 showing a variation in which the direction to compress or extend the container 10 according to the second embodiment is changed.

Moreover, it is possible to change the direction to compress or extend the container 10. FIG. 8 is a plan view of the container 10 showing a variation in which the direction to compress or extend the container 10 according to the second embodiment is changed. Though the above-described direction in which the container 10 is compressed or extended is the Z direction, the direction may be the Y direction (direction orthogonal to the Z direction) as shown in FIG. 8. In this case, the direction in which the terahertz wave is made incident is the Y direction or an X direction.

After the container 10 is arranged such that the predetermined direction (Y direction) is parallel with or orthogonal to the direction in which the terahertz wave is made incident (Y direction or Z direction), the average refractive index of the container 10 is adjusted by compressing or extending the container 10 so that an optical path of the terahertz wave incident to the container 10 and an optical path of the terahertz wave which has transmitted through the container 10 and the DUT 1 are aligned on a straight line.

Moreover, after the container 10 is disposed such that the predetermined direction (Y direction) is parallel with or orthogonal to the direction (Y direction or the X direction) in which the terahertz wave is made incident, the DUT 1 will be measured.

In the variation shown in FIG. 8, the first structures 100 are in a form of a flat plate, and do not include a first gap portion 11'. It should be noted that some of the first structures 100 are penetrated by a through gap portion 110 extending in the Z direction. The extending direction (Z direction) of this through gap portion 110 and the predetermined direction (Y direction) in which the first structures 100 are piled up intersect with each other at the right angle. At least a part of the DUT 1 is disposed in the through gap portion 110 as described before.

It should be noted that the spacers 18 are arranged at four corners of the first structure 100 as in the second embodiment (refer to FIG. 7(c)).

Third Embodiment

The container 10 according to the third embodiment is different from the container 10 according to the second embodiment in that a second structure 13 is provided in place of the spacers (interval maintaining member) 18 according to the second embodiment.

Figure 22:
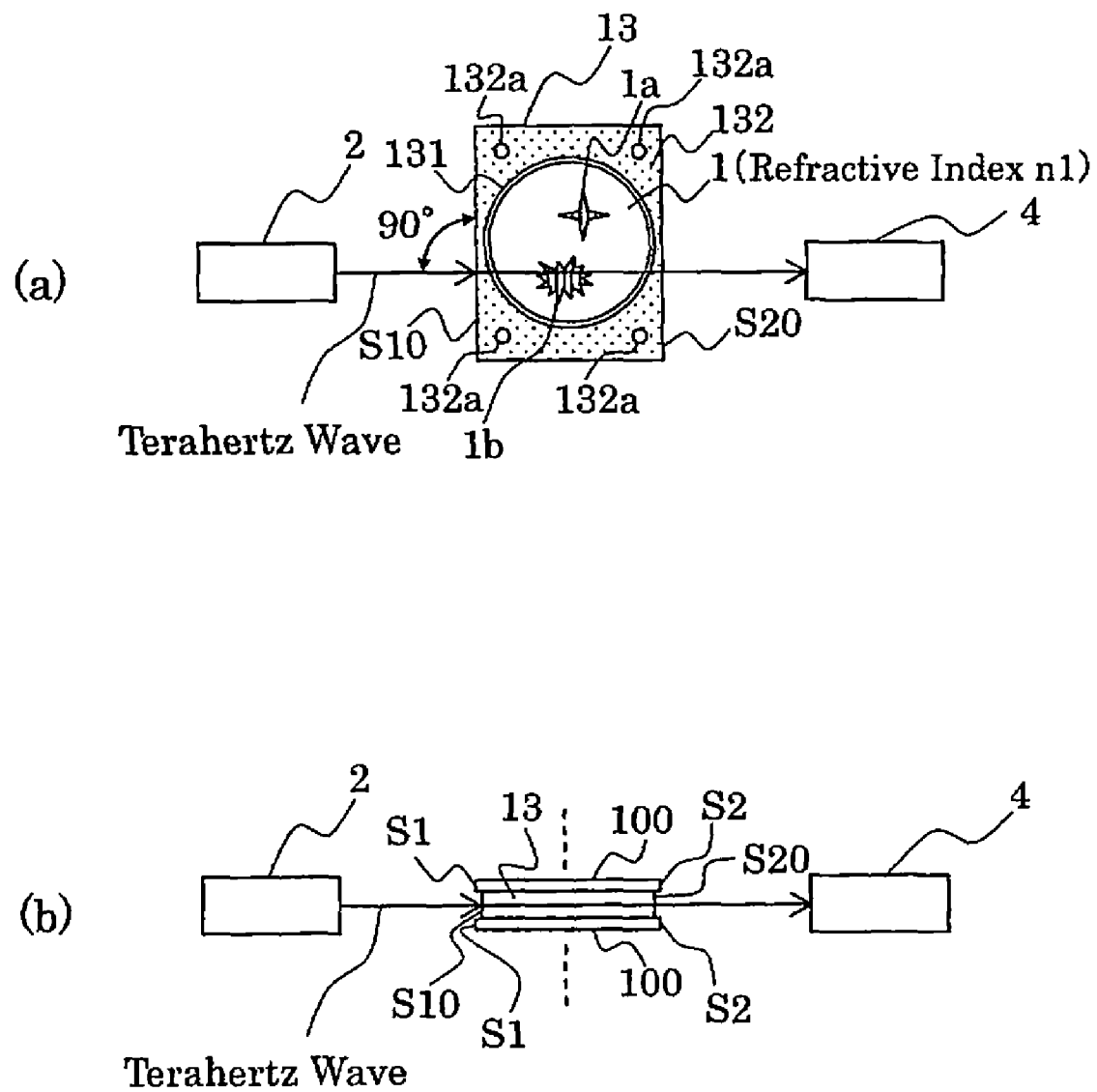
Figure 23:
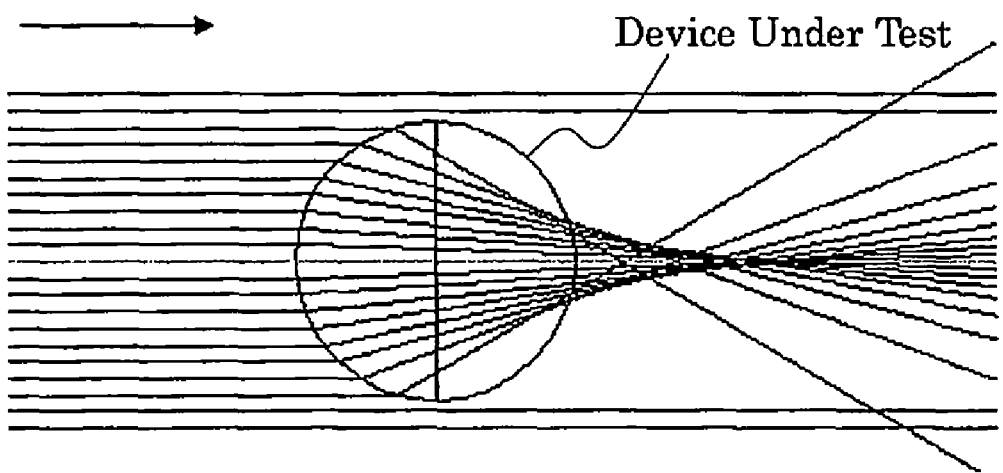
FIG. 23 shows estimated optical paths of the terahertz wave when the refractive index of a conventional device under test is 1.4, and the refractive index of the ambient air of the device under test is 1.

FIGS. 22(a) and 22(b) are views of a state in which at least a part of the DUT 1 is stored in the container 10 according to the third embodiment, and the terahertz wave is irradiated on the container 10, in which FIG. 22(a) is a plan view and FIG. 22(b) is a partial front view. It should be noted that the upper pressing member 16a, the bolt head portions 14a, and the bolt thread portions 14c are not shown in FIG. 22(a). FIG. 22(b) only shows a neighborhood of a position through which the terahertz wave transmits. It should be noted that FIG. 22(a) is approximately the same as FIG. 4 (when the enclosure portion 12 is replaced by the second structure 13). Moreover, the terahertz wave output device 2 and the terahertz wave detector 4 included in the terahertz wave measurement device (electromagnetic wave measurement device) are the same as those of the first embodiment. The frequency of the electromagnetic wave output and detected by the terahertz wave measurement device (electromagnetic wave measurement device) is the same as that of the first embodiment.

The first structure 100 is the same as that of the second embodiment, and hence a description thereof is omitted.

A second gap portion 131 and a second enclosure portion 132 included by the second structure 13 are configured in the same way as the gap portion 11 and the enclosure portion 12 according to the first embodiment, and hence a description thereof is omitted. It should be noted that a material of the second structure 13 may be the same as the material of the enclosure portion 12 according to the first embodiment (such as a foamable resin). It should be noted that a third flat surface portion S10 and a fourth flat surface portion S20 included by the second enclosure portion 132 correspond to the first flat surface portion S1 and the second flat surface portion S2 of the enclosure portion 12 according to the first embodiment.

FIGS. 9(a), 9(b), and 9(c) are views of the container 10 according to the third embodiment, in which FIG. 9(a) is a plan view, FIG. 9(b) is a front view, and FIG. 9(c) is a plan view without the upper pressing member 16a, the bolt head portions 14a, and the bolt thread portions 14c. The container 10 according to the third embodiment is provided with the first structures 100 and the second structures 13.

The second structure 13 is disposed between the multiple first structures 100.

The average refractive index n2 of the container 10 can be changed by changing the predetermined intervals H3 (=thickness of the second structure 13). According to the third embodiment, the predetermined intervals H3 are changed by compressing or extending the container 10. Specifically, the refractive index of the container 10 is changed by clamping the enclosure portion 12 using the upper pressing member 16a and the lower pressing member 16b, thereby changing the predetermined intervals H3.

On this occasion, the refractive index of the DUT 1 is denoted by n1, and the average refractive index of the container 10 is denoted by n2. Then, n2 can be adjusted so that the relationship $n1-0.1 \leq n2 \leq n1+0.1$ holds. It is preferable that the relationship $n1=n2$ holds. Moreover, n1 and n2 may not be equal to the refractive index (such as 1) of ambient air of the container 10.

Referring to FIG. 9(b), the upper pressing member 16a is placed on a top of the uppermost second structure 13. A lower pressing member 16b is placed on a bottom of the lowest second structure 13. The bolt head portion 14a is placed on a top of the upper pressing member 16a. The bolt thread portion 14c is integrated with the bolt head portion 14a, and a male thread is provided thereupon. The bolt thread portion 14c passes through (the through holes 12'a of) the first structures 100, (the through holes 132a of) the second structures 13 (refer to FIGS. 21, 22(a), and 22(b)), the upper pressing member 16a, and the lower pressing member 16b. Nuts 14b are provided on a bottom surface of the lower pressing member 16b. The bolt thread portion 14c is threaded into the nut 14b.

Referring to FIG. 9(c), a contour of a bottom surface of the second structure 13 is a rectangle slightly smaller than a contour of a bottom surface of the first structure 100.

On this occasion, the predetermined intervals H3 can be reduced by turning the bolt head portions 14a to tighten the thread (of the bolt thread portions 14c) while the nuts 14b are fixed so as not to turn, thereby compressing the second structures 13 of the container 10. It should be noted that the predetermined intervals H3 can be increased by loosening the thread (of the bolt thread portions 14c), thereby extending the second structures 13 of the container 10.

Moreover, the average refractive index n2 of the container 10 in the state shown in FIG. 9(b) is represented by the following equations (4) and (5). It should be noted that n2' denotes a refractive index of the first structure 100. It is assumed that a refractive index of the second structure 13 is n3. Moreover, each of the predetermined intervals H3 are equal. In other words, it is assumed that the multiple first structures 100 are arranged at the equal interval. Moreover, H4 denotes a height of the second structure 13 when the second structure 13 is neither compressed nor extended. Further, n3o denotes a refractive index of the second structure 13 when the second structure 13 is neither compressed nor extended.

$$n2 = 1 + ((n2'-1) \times H2 + (n3-1) \times H3)/(H2+H3) \quad (4)$$
$$= 1 + ((n2'-1) \times H2 + (n3o-1) \times H4)/(H2+H3) \quad (5)$$

As in the equation (1), a relationship represented by the following equation (6) holds between n3o and n3, and the equations (4) and (5) are thus equal to each other.

$$n3o = 1 + (n3-1) \times H3/H4 \quad (6)$$

It should be noted that the predetermined intervals H3 may be different from each other.

Moreover, the direction to compress or extend the container 10 is a direction of the height of the container 10 (Z direction, refer to FIGS. 14(a), 14(b), 15(a), and 15(b)).

Moreover, as in the first embodiment, referring to FIGS. 22(a) and 22(b), a direction of the normal line of the first flat surface portion S1 is parallel with the travel direction of the terahertz wave output from the terahertz wave output device 2 of the terahertz wave measurement device toward the DUT 1. The container 10 is provided as described above so as to measure the DUT 1 by the terahertz wave measurement device. The terahertz wave output toward the DUT 1 may be made incident to the first flat surface portion S1 of the first structures 100, or the first flat surface portion S1 of the second structures 13.

When the terahertz wave output from the terahertz wave output device 2 is supplied to the container 10, a Bragg reflection may occur depending on the frequency of the terahertz wave. In this case, the terahertz wave hardly transmits through the container 10, and the Bragg reflection is thus preferably avoided.

The frequency $f_N$ (of the electromagnetic wave supplied to the container 10) which causes the Bragg reflection is represented by the above-mentioned equation (3).

On this occasion, the predetermined interval H3 is determined such that the frequency of the terahertz wave supplied to the container 10 is not close to the frequency $f_N$. In other words, the predetermined interval H3 is determined such that the terahertz wave does not present the Bragg reflection. The determination is carried out as in the second embodiment.

A description will now be given of an operation of the third embodiment.

Figure 21:
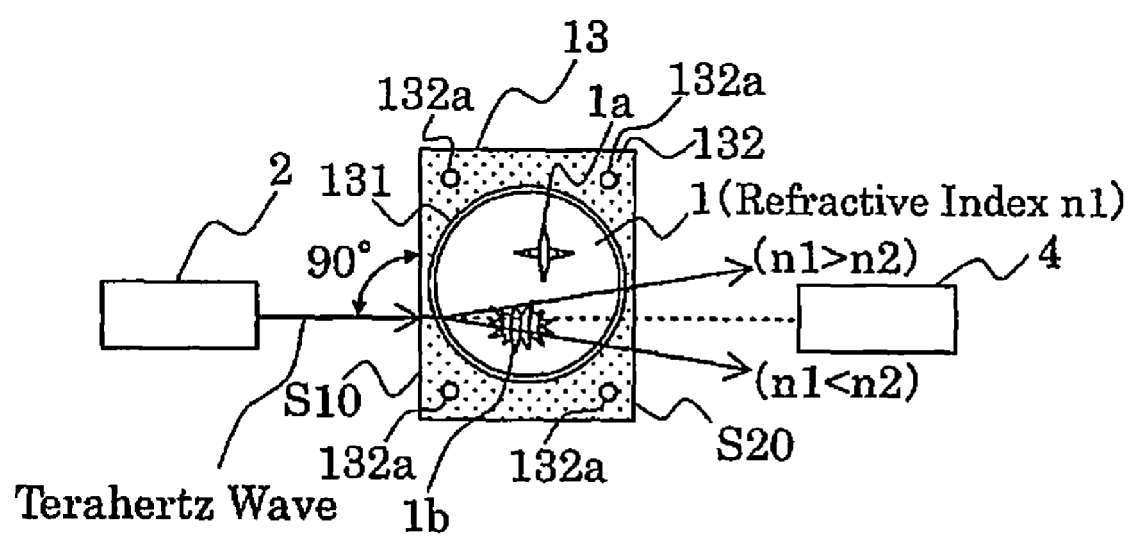
FIG. 21 illustrates the adjustment of the average refractive index n2 of the container 10 according to the third embodiment.

FIG. 21 illustrates the adjustment of the average refractive index n2 of the container 10 according to the third embodiment. It should be noted that the upper pressing member 16a, the bolt head portions 14a, and the bolt thread portions 14c are not shown in FIG. 21.

Referring to FIG. 21, the refractive index n2 of the container 10 is first adjusted (as in the second embodiment).

Then, referring to FIGS. 22(a) and 22(b), the DUT 1 is measured (as in the second embodiment).

According to the third embodiment, there are obtained the same effects as in the second embodiment.

Moreover, compared with the spacers 18 according to the second embodiment, the second structures 13 according to the third embodiment can support wider areas of the first structures 100. As a result, according to the third embodiment, the intervals between the first structures 100 can be equalized at any portions (such as a portion slightly close to the center) of the first structures 100 more easily than in the second embodiment.

Further, according to the third embodiment, since a strength of the container 10 is increased by the second structures 13, a thickness of the first structures 100 according to the third embodiment can be reduced compared with the thickness of the first structures 100 according to the second embodiment. Consequently, the frequency $f_N$ which causes the Bragg reflection can be increased. Therefore, the frequency $f_1$ can easily be set sufficiently higher than the frequency of the terahertz wave supplied to the container 10, and it is thus possible to easily prevent adverse influence on the measurement.

It should be noted that the container 10 can be compressed or extended using the frames 14d as shown in FIG. 5 in the container 10 according to the third embodiment.

Figure 10:
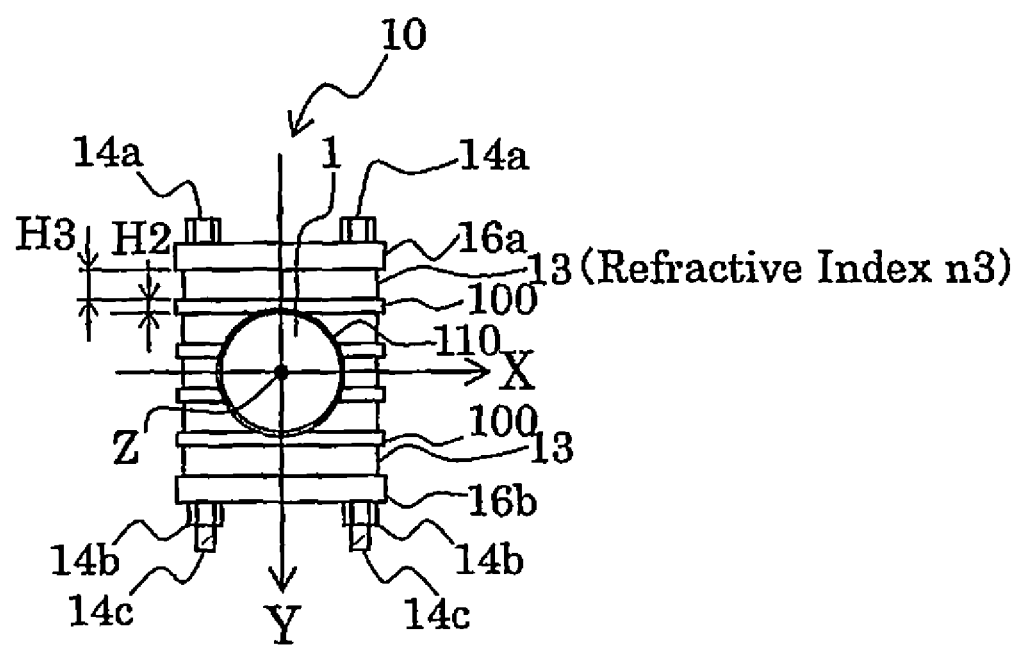
FIG. 10 is a plan view of the container 10 showing a variation in which the direction to compress or extend the container 10 according to the third embodiment is changed.

Moreover, it is possible to change the direction to compress or extend the container 10. FIG. 10 is a plan view of the container 10 showing a variation in which the direction to compress or extend the container 10 according to the third embodiment is changed. Though the above-described direction in which the container 10 is compressed or extended is the Z direction, the direction may be the Y direction (direction orthogonal to the Z direction) as shown in FIG. 10. In this case, the direction in which the terahertz wave is made incident is the Y direction or an X direction.

After the container 10 is arranged such that the predetermined direction (Y direction) is parallel with or orthogonal to the direction in which the terahertz wave is made incident (Y direction or Z direction), the average refractive index of the container 10 is adjusted by compressing or extending the container 10 so that an optical path of the terahertz wave incident to the container 10 and an optical path of the terahertz wave which has transmitted through the container 10 and the DUT 1 are aligned on a straight line.

Moreover, after the container 10 is disposed such that the predetermined direction (Y direction) is parallel with or orthogonal to the direction (Y direction or the X direction) in which the terahertz wave is made incident, the DUT 1 will be measured.

In the variation shown in FIG. 10, the first structures 100 are in a form of a flat plate, the second structures 13 is in a form of a rectangular solid, and the first structures 100 and the second structures 13 do not include the gap portion 11. It should be noted that some of the first structures 100 and the second structures 13 are penetrated by the through gap portion 110 extending in the Z direction. The extending direction (Z direction) of this through gap portion 110 and the predetermined direction (Y direction) in which the first structures 100 are piled up intersect with each other at the right angle. At least a part of the DUT 1 is disposed in the through gap portion 110 as described before.

Fourth Embodiment

A fourth embodiment is a method for scanning the DUT 1 in the horizontal direction (X direction) using the container 10 according to the first to third embodiments.

The configurations of the container 10 and the terahertz wave measurement device according to the fourth embodiment are the same as those according to the first to third embodiments, and hence a description thereof is omitted.

A description will now be given of an operation of the fourth embodiment. FIGS. 11(a) and 11(b) are plan views of the container 10 and the terahertz wave measurement device for describing the operation of the fourth embodiment. It should be noted that the bolt head portions 14a, the upper pressing member 16a, and the through holes 12a according to the first embodiment are not shown. The bolt head portions 14a and the through holes 12'a through which the bolt thread portions 14c pass according to the second embodiment are not shown. The upper pressing member 16a, the second structures 13, the bolt head portions 14a, and the through holes 12'a through which the bolt thread portions 14c pass according to the third embodiment are not shown. When the DUT 1 is scanned in the horizontal direction (X direction) using the container 10 according to the second and third embodiments, the container 10 in FIGS. 11(a) and 11(b) is the first structure 100.

Referring to FIG. 11(a), the terahertz wave output device 2 of the terahertz wave measurement device outputs the terahertz wave (referred to as "output step" hereinafter). The output terahertz wave transmits through the enclosure portion 12 and the DUT 1 while traveling straight as described in the first, second, and third embodiments, and is detected by the terahertz wave detector 4 of the terahertz wave measurement device (referred to as "detection step" hereinafter). As a result, the DUT 1 is measured by the terahertz wave measurement device. Referring to FIG. 11(a), the terahertz wave transmits through the content 1b, and thus, the position and the like of the content 1b are revealed according to a result of the detection of the terahertz wave.

It should be noted that optical paths of the terahertz wave are denoted by P1 and P2. The optical path P1 is a path of the terahertz wave starting from the output of the terahertz wave from the terahertz wave output device 2 to the incident to the container 10. The optical path P2 is a path of the terahertz wave starting from the transmission of the terahertz wave through the enclosure portion 12 and the DUT 1 to the arrival to the terahertz wave detector 4.

During the output step and the detection step, the container 10 and the DUT 1 move horizontally (downward in FIGS.

Figure 11:
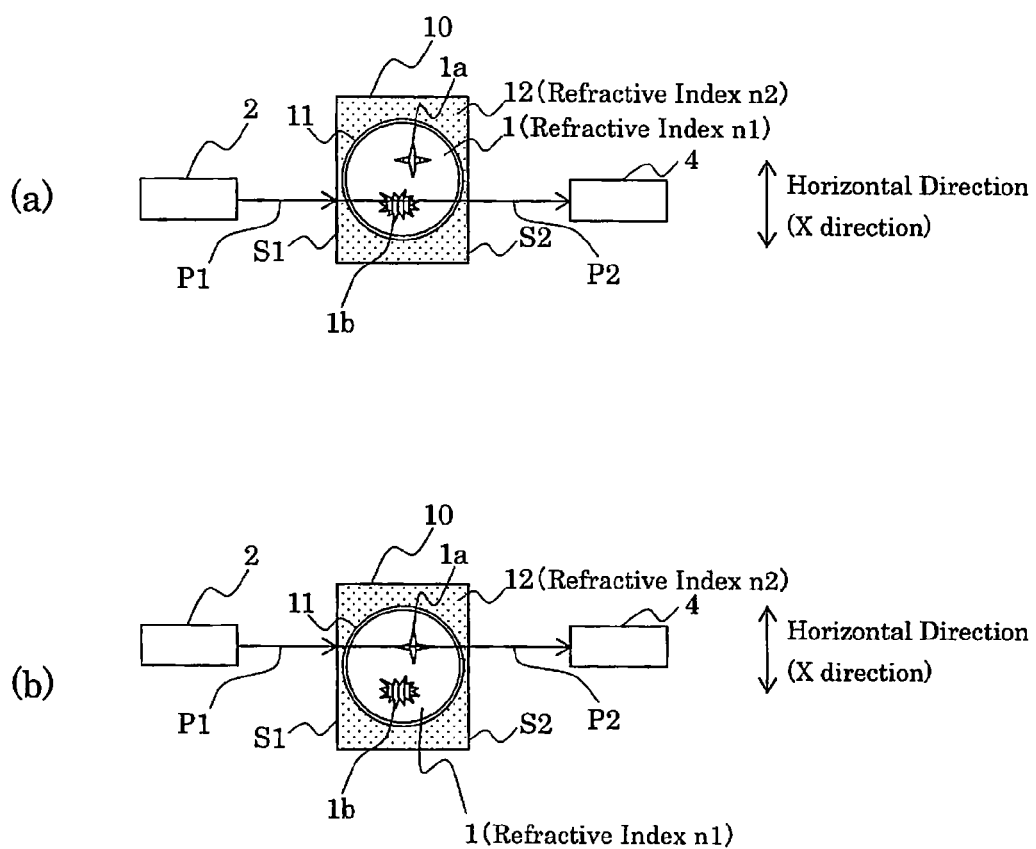
FIGS. 11(a) and 11(b) are plan views of the container 10 and the terahertz wave measurement device for describing the operation of the fourth embodiment.

11(*a*) and 11(*b*)) with respect to the optical paths P1 and P2 of the terahertz wave. Then, the optical path P2 intersects with the content 1*a* as shown in FIG. 11(*b*). The terahertz wave transmits through the content 1*a*, and thus, the position and the like of the content 1*a* are revealed according to a result of the detection by the terahertz wave.

According to the fourth embodiment, the DUT 1 can be scanned in the horizontal direction (X direction). As a result, the DUT 1 can be tomographically measured.

A similar effect can be provided if the optical paths P1 and P2 of the terahertz wave move horizontally (upward in FIGS. 11(*a*) and 11(*b*)) with respect to the container 10 and the DUT 1 during the output step and the detection step. In order to move the optical paths P1 and P2 of the terahertz wave, the terahertz wave output device 2 and the terahertz wave detector 4 may be moved.

Fifth Embodiment

The fifth embodiment is a method for scanning the DUT 1 using the container 10 according to the first to third embodiments while the DUT 1 is rotated.

The configurations of the container 10 and the terahertz wave measurement device according to the fifth embodiment are the same as those according to the first to third embodiments, and hence a description thereof is omitted.

Figure 12:
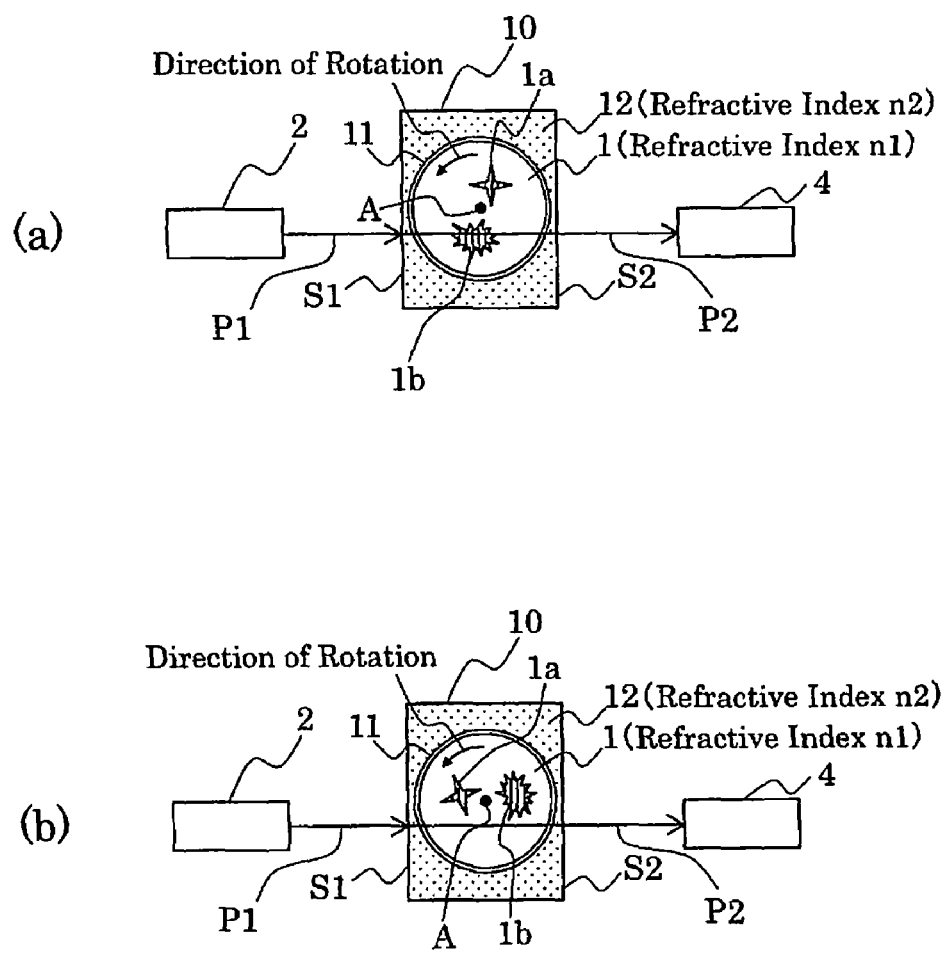
FIGS. 12(a) and 12(b) are plan views of the container 10 and the terahertz wave measurement device for describing the operation of the fifth embodiment.

A description will now be given of an operation of the fifth embodiment. FIGS. 12(*a*) and 12(*b*) are plan views of the container 10 and the terahertz wave measurement device for describing the operation of the fifth embodiment. It should be noted that the definitions of the output step, the detection step, the definitions of the optical paths P1 and P2, and items not shown in FIGS. 12(*a*) and 12(*b*) are the same as those of the fourth embodiment. Moreover, when the DUT 1 is scanned using the container 10 according to the second and third embodiments, the container 10 in FIGS. 12(*a*) and 12(*b*) is the first structure 100 as in the fourth embodiment.

Referring to FIG. 12(*a*), the output step is carried out. The output terahertz wave transmits through the enclosure portion 12 and the DUT 1 while traveling straight as described in the first embodiment. Then, the detection step is carried out. As a result, a certain part of the DUT 1 is measured by the terahertz wave measurement device.

Figure 14:
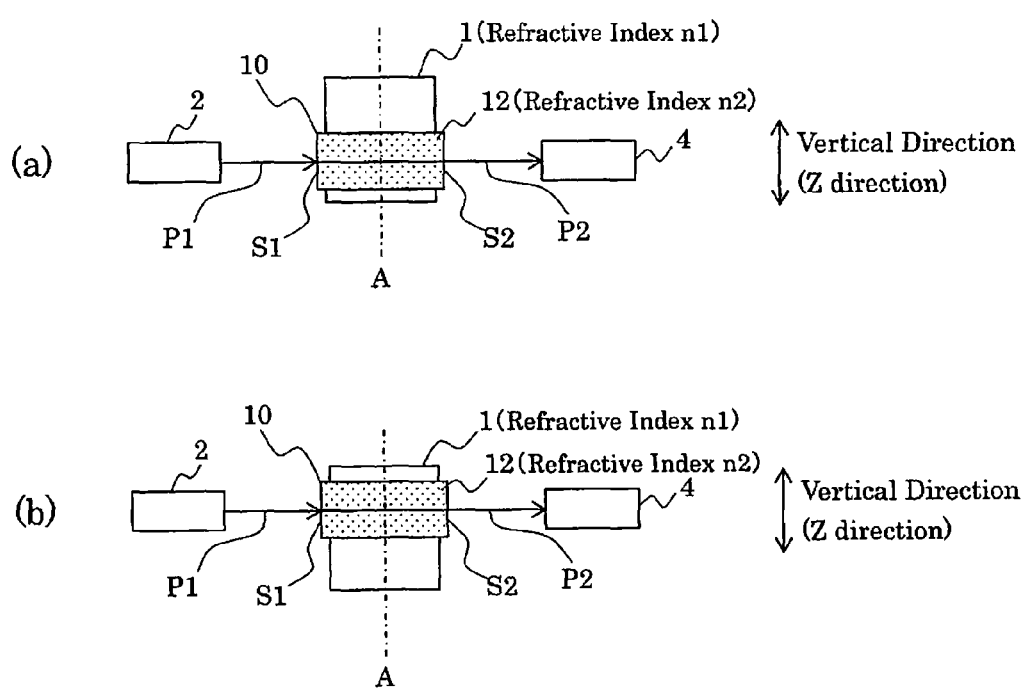
FIGS. 14(a) and 14(b) are front views of the container 10 and the terahertz wave measurement device according to the seventh embodiment.

While the output step and the detection step are carried out, the DUT 1 is rotated about a line A extending vertically (Z direction) (refer to FIGS. 14(*a*), 14(*b*), 15(*a*), and 15(*b*)) as a rotational axis (line A may not be a real member). For example, the DUT 1 is rotated counterclockwise. Then, the DUT 1 reaches an arrangement shown in FIG. 12(*b*). The part of the DUT 1 which intersects with the optical path P2 is different between the case in FIG. 12(*b*) and the case in FIG. 12(*a*). Thus, the case in FIG. 12(*b*) and the case in FIG. 12(*a*) can respectively measure different parts of the DUT 1.

According to the fifth embodiment, the DUT 1 can be scanned while the DUT 1 is being rotated. As a result, the DUT 1 can be tomographically measured.

When the DUT 1 is scanned using the container 10 according to the first embodiment (refer to FIG. 2), the DUT 1 receives the terahertz wave while rotating about the predetermined rotational axis (the line A in the Z direction, refer to FIGS. 14(*a*), 14(*b*), 15(*a*), and 15(*b*)), and the enclosure portion 12 will be compressed or extended in the Z direction.

Moreover, when the DUT 1 is scanned using the container 10 according to the variation of the first embodiment (refer to FIG. 6), the DUT 1 receives the terahertz wave while rotating about the predetermined rotational axis (the line A in the Z direction, refer to FIGS. 14(*a*), 14(*b*), 15(*a*), and 15(*b*)), and the enclosure portion 12 will be compressed or extended in the Y direction. This Y direction is the direction in which the terahertz wave is made incident (when the direction in which the terahertz wave is made incident is the Y direction), or the direction orthogonal to the Z direction and the optical path of the terahertz wave (when the direction in which the terahertz wave is made incident is the X direction).

Figure 7:
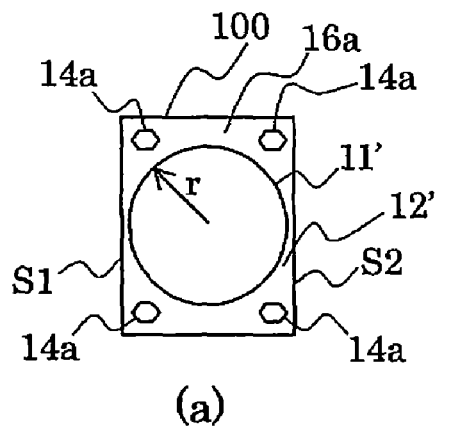
Figure 7:
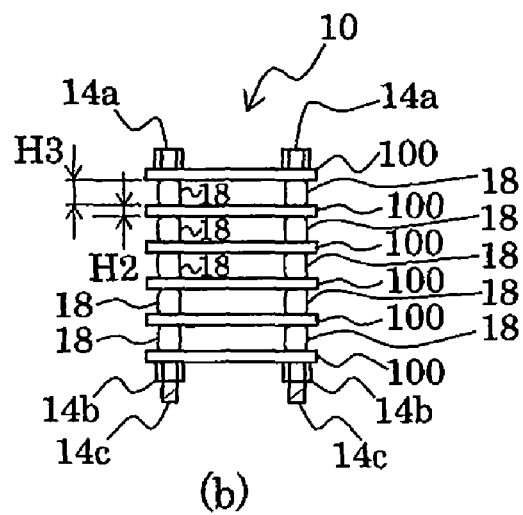
Figure 7:
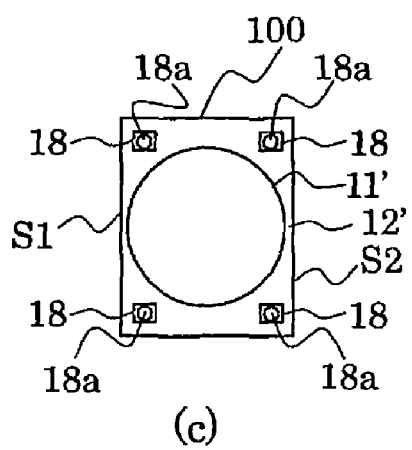

When the DUT 1 is scanned using the container 10 according to the second embodiment (refer to FIGS. 7(*a*), 7(*b*), and 7(*c*)), the DUT 1 receives the terahertz wave while rotating about the predetermined rotational axis (the line A in the Z direction, refer to FIGS. 14(*a*), 14(*b*), 15(*a*), and 15(*b*)), and the container 10 will be compressed or extended in the Z direction.

Moreover, when the DUT 1 is scanned using the container 10 according to the variation of the second embodiment (refer to FIG. 8), the DUT 1 receives the terahertz wave while rotating about the predetermined rotational axis (the line A in the Z direction, refer to FIGS. 14(*a*), 14(*b*), 15(*a*), and 15(*b*)), and the container 10 will be compressed or extended in the Y direction. This Y direction is the direction in which the terahertz wave is made incident (when the direction in which the terahertz wave is made incident is the Y direction), or the direction orthogonal to the Z direction and the optical path of the terahertz wave (when the direction in which the terahertz wave is made incident is the X direction).

Figure 9:
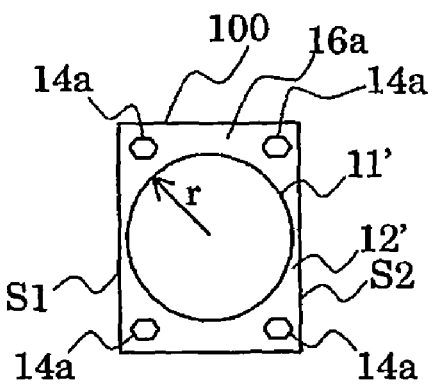
Figure 9:
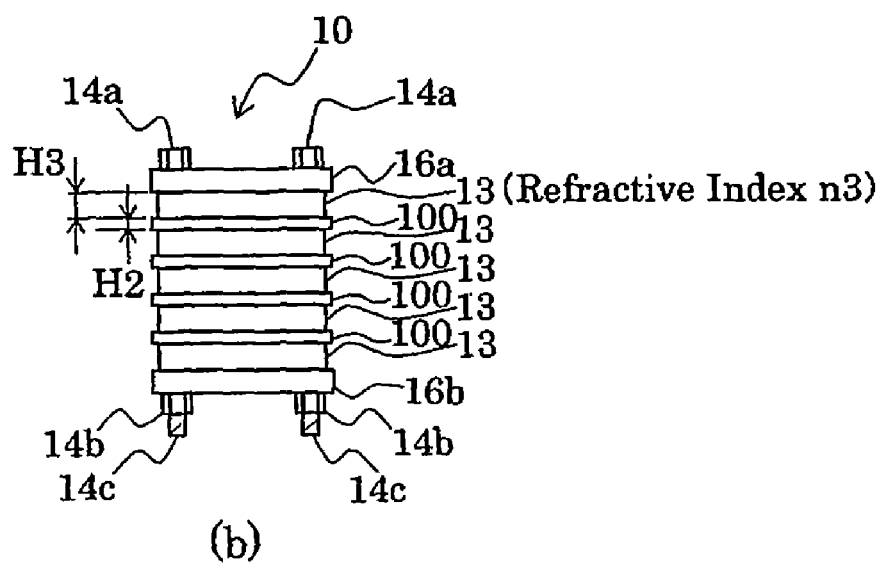
Figure 9:
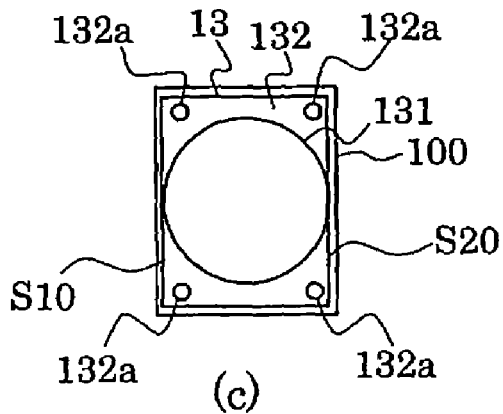

When the DUT 1 is scanned using the container 10 according to the third embodiment (refer to FIGS. 9(*a*), 9(*b*), and 9(*c*)), the DUT 1 receives the terahertz wave while rotating about the predetermined rotational axis (the line A in the Z direction, refer to FIGS. 14(*a*), 14(*b*), 15(*a*), and 15(*b*)), and the container 10 will be compressed or extended in the Z direction.

Moreover, when the DUT 1 is scanned using the container 10 according to the variation of the third embodiment (refer to FIG. 10), the DUT 1 receives the terahertz wave while rotating about the predetermined rotational axis (the line A in the Z direction, refer to FIGS. 14(*a*), 14(*b*), 15(*a*), and 15(*b*)), and the container 10 will be compressed or extended in the Y direction. This Y direction is the direction in which the terahertz wave is made incident (when the direction in which the terahertz wave is made incident is the Y direction), or the direction orthogonal to the Z direction and the optical path of the terahertz wave (when the direction in which the terahertz wave is made incident is the X direction).

Sixth Embodiment

A sixth embodiment is a method for scanning the DUT 1 while the container 10 and the optical paths P1 and P2 of the terahertz wave are rotated using the container 10 according to the first to third embodiments.

The configurations of the container 10 and the terahertz wave measurement device according to the sixth embodiment are the same as those according to the first to third embodiments, and hence a description thereof is omitted.

Figure 13:
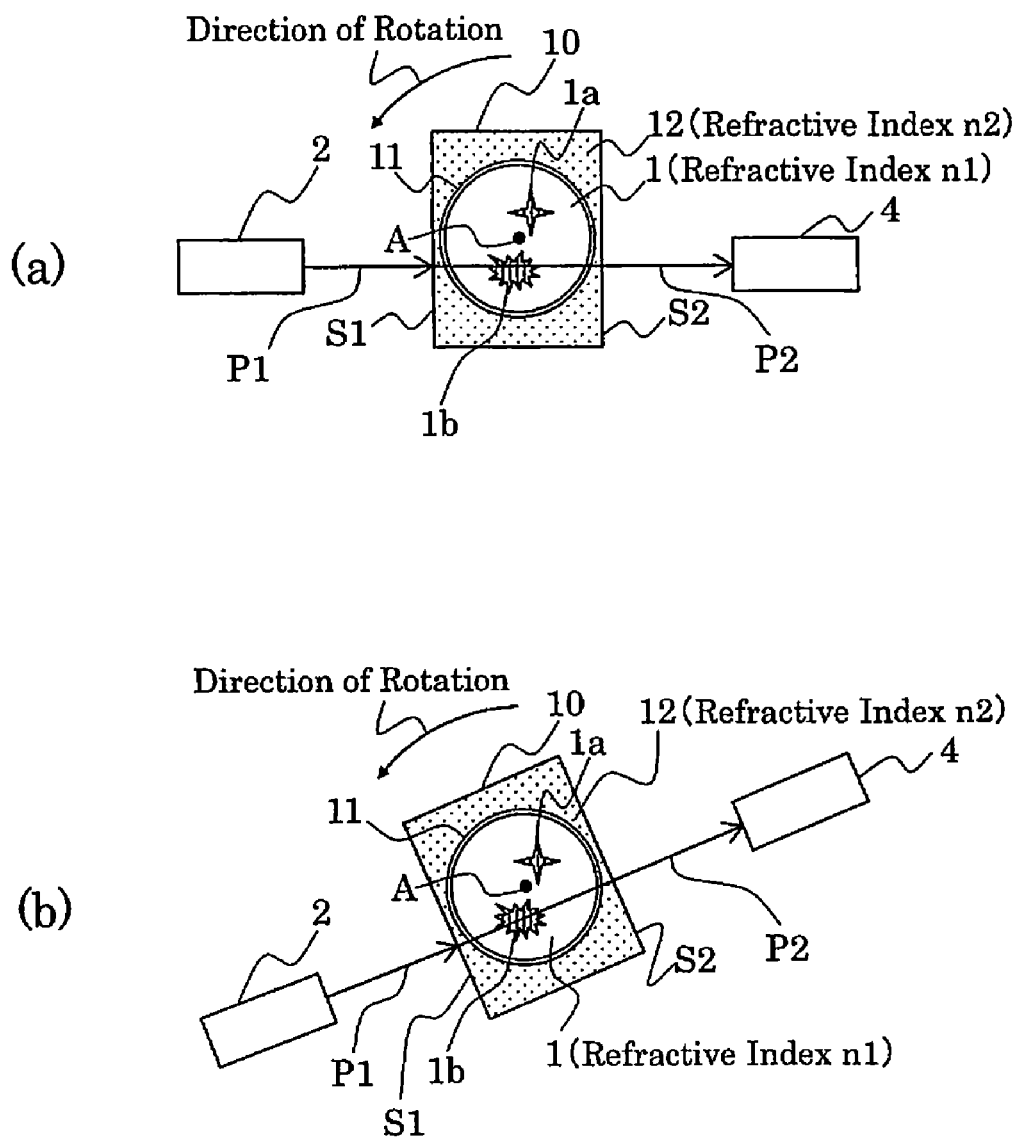
FIGS. 13(a) and 13(b) are plan views of the container 10 and the terahertz wave measurement device for describing the operation of the sixth embodiment.

A description will now be given of an operation of the sixth embodiment. FIGS. 13(*a*) and 13(*b*) are plan views of the container 10 and the terahertz wave measurement device for describing the operation of the sixth embodiment. It should be noted that the definitions of the output step, the detection step, the definitions of the optical paths P1 and P2, and items not shown in FIGS. 13(*a*) and 13(*b*) are the same as those of the fourth embodiment. Moreover, when the DUT 1 is scanned using the container 10 according to the second and third embodiments, the container 10 in FIGS. 13(*a*) and 13(*b*) is the first structure 100 as in the fourth embodiment.

Referring to FIG. 13(a), the output step is carried out. The output terahertz wave transmits through the enclosure portion 12 and the DUT 1 while traveling straight as described in the first embodiment. Then, the detection step is carried out. As a result, a certain part of the DUT 1 is measured by the terahertz wave measurement device.

While the output step and the detection step are carried out, the container 10 and the optical paths P1 and P2 of the terahertz wave are rotated about the line A extending vertically (Z direction) (refer to FIGS. 14(a), 14(b), 15(a), and 15(b)) as a rotational axis. For example, they may be rotated counterclockwise. Then, the DUT 1 reaches an arrangement shown in FIG. 13(b). The part of the DUT 1 which intersects with the optical path P2 is different between the case in FIG. 13(b) and the case in FIG. 13(a). Thus, the case in FIG. 13(b) and the case in FIG. 13(a) can respectively measure different parts of the DUT 1.

According to the sixth embodiment, the DUT 1 can be scanned while the container 10 and the optical paths P1 and P2 of the terahertz wave are rotated. As a result, the DUT 1 can be tomographically measured.

When the DUT 1 is scanned using the container 10 according to the first embodiment (refer to FIG. 2), the DUT 1 receives the terahertz wave while the container 10 and the optical paths P1 and P2 of the terahertz wave are rotated about the predetermined rotational axis (the line A in the Z direction, refer to FIGS. 14(a), 14(b), 15(a), and 15(b)), and the enclosure portion 12 will be compressed or extended in the Z direction.

Moreover, when the DUT 1 is scanned using the container 10 according to the variation of the first embodiment (refer to FIG. 6), the DUT 1 receives the terahertz wave while the container 10 and the optical paths P1 and P2 of the terahertz wave are rotated about the predetermined rotational axis (the line A in the Z direction, refer to FIGS. 14(a), 14(b), 15(a), and 15(b)), and the enclosure portion 12 will be compressed or extended in the Y direction. This Y direction is the direction in which the terahertz wave is made incident (when the direction in which the terahertz wave is made incident is the Y direction), or the direction orthogonal to the Z direction and the optical path of the terahertz wave (when the direction in which the terahertz wave is made incident is the X direction).

When the DUT 1 is scanned using the container 10 according to the second embodiment (refer to FIGS. 7(a), 7(b), and 7(c)), the DUT 1 receives the terahertz wave while the container 10 and the optical paths P1 and P2 of the terahertz wave are rotated about the predetermined rotational axis (the line A in the Z direction, refer to FIGS. 14(a), 14(b), 15(a), and 15(b)), and the container 10 will be compressed or extended in the Z direction.

Moreover, when the DUT 1 is scanned using the container 10 according to the variation of the second embodiment (refer to FIG. 8), the DUT 1 receives the terahertz wave while the container 10 and the optical paths P1 and P2 of the terahertz wave are rotated about the predetermined rotational axis (the line A in the Z direction, refer to FIGS. 14(a), 14(b), 15(a), and 15(b)), and the container 10 will be compressed or extended in the Y direction. This Y direction is the direction in which the terahertz wave is made incident (when the direction in which the terahertz wave is made incident is the Y direction), or the direction orthogonal to the Z direction and the optical path of the terahertz wave (when the direction in which the terahertz wave is made incident is the X direction).

When the DUT 1 is scanned using the container 10 according to the third embodiment (refer to FIGS. 9(a), 9(b), and 9(c)), the DUT 1 receives the terahertz wave while the container 10 and the optical paths P1 and P2 of the terahertz wave are rotated about the predetermined rotational axis (the line A in the Z direction, refer to FIGS. 14(a), 14(b), 15(a), and 15(b)), and the container 10 will be compressed or extended in the Z direction.

Moreover, when the DUT 1 is scanned using the container 10 according to the variation of the third embodiment (refer to FIG. 10), the DUT 1 receives the terahertz wave while the container 10 and the optical paths P1 and P2 of the terahertz wave are rotated about the predetermined rotational axis (the line A in the Z direction, refer to FIGS. 14(a), 14(b), 15(a), and 15(b)), and the container 10 will be compressed or extended in the Y direction. This Y direction is the direction in which the terahertz wave is made incident (when the direction in which the terahertz wave is made incident is the Y direction), or the direction orthogonal to the Z direction and the optical path of the terahertz wave (when the direction in which the terahertz wave is made incident is the X direction).

Seventh Embodiment

A seventh embodiment is a method for scanning the DUT 1 in the vertical direction (Z direction) using the container 10 according to the first to third embodiments.

FIGS. 14(a) and 14(b) are front views of the container 10 and the terahertz wave measurement device according to the seventh embodiment. Configurations of the container 10 and the terahertz wave measurement device according to the seventh embodiment are approximately the same as those according to the first to third embodiments. It should be noted that the DUT 1 is cylindrical, and a part of the DUT 1 is stored in the gap portion 11 (or the through gap portion 110) of the container 10.

It should be noted that the bolt head portions 14a, the nuts 14b, the bolt thread portions 14c, the upper pressing member 16a, and the lower pressing member 16b according to the first embodiment are not shown in FIGS. 14(a) and 14(b). The bolt head portions 14a, the nuts 14b, and the bolt thread portions 14c according to the second embodiment are not shown. The bolt head portions 14a, the nuts 14b, the bolt thread portions 14c, the upper pressing member 16a, and the lower pressing member 16b according to the third embodiment are not shown. When the container 10 according to the second and third embodiments is used to scan the DUT 1, the enclosure portion 12 in FIGS. 14(a) and 14(b) schematically shows the shape of the container 10 (simply shows a rough contour of the container 10, and does not show the respective first structures 100 and the like).

A description will now be given of an operation of the seventh embodiment. It should be noted that the definitions of the output step, the detection step, and the definitions of the optical paths P1 and P2 are the same as those of the fourth embodiment.

Referring to FIG. 14(a), the output step is carried out. The output terahertz wave transmits through the enclosure portion 12 and the DUT 1 while traveling straight as described in the first embodiment. Then, the detection step is carried out. As a result, a lower part of the DUT 1 is measured by the terahertz wave measurement device.

During the output step and the detection step, the container 10 and the optical paths P1 and P2 of the terahertz wave move vertically (upward in FIGS. 14(a) and 14(b)) with respect to the DUT 1. Then, the optical path P2 intersects with an upper part of the DUT 1 as shown in FIG. 14(b). As a result, the upper part of the DUT 1 is measured by the terahertz wave measurement device. It should be noted that, in order to move the optical paths P1 and P2 of the terahertz wave, the terahertz wave output device 2 and the terahertz wave detector 4 may be moved.

According to the seventh embodiment, the DUT 1 can be scanned in the vertical direction (Z direction). As a result, the DUT 1 can be tomographically measured.

During the output step and the detection step, the DUT 1 may move vertically with respect to the container 10 and the optical paths P1 and P2 of the terahertz wave.

Eighth Embodiment

An eighth embodiment is a method for scanning the DUT 1 in the vertical direction (Z direction) using the container 10 according to the first to third embodiments.

Figure 15:
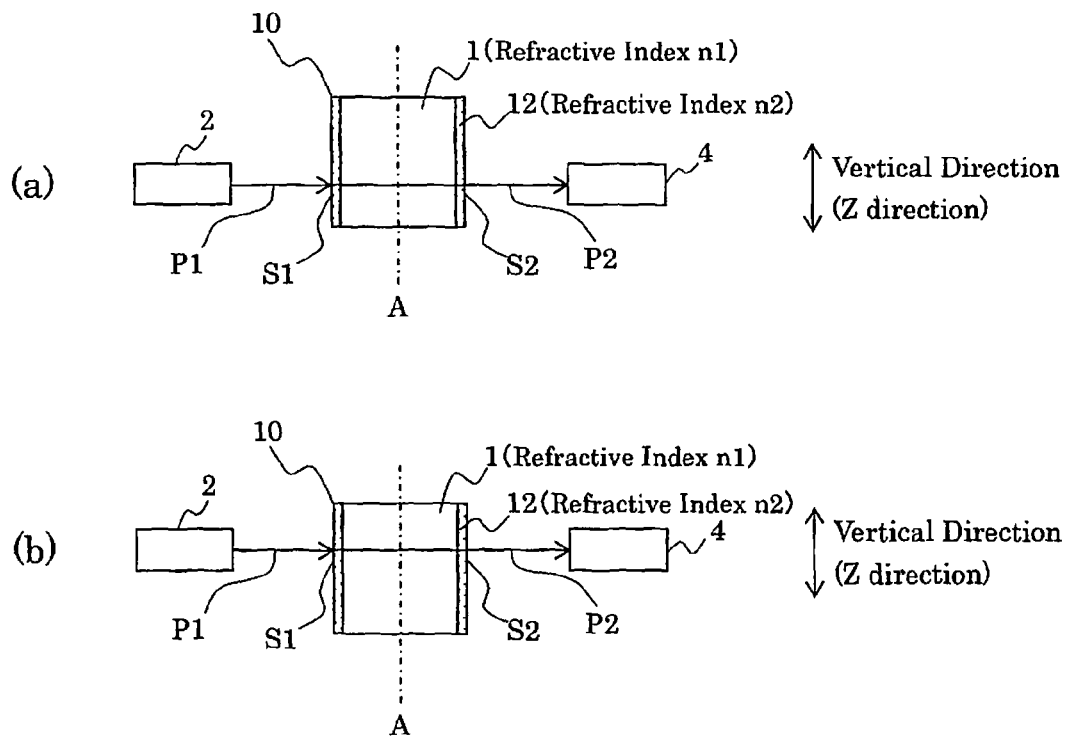
FIGS. 15(a) and 15(b) are front views of the container 10 and the terahertz wave measurement device according to the eighth embodiment.

FIGS. 15(a) and 15(b) are front views of the container 10 and the terahertz wave measurement device according to the eighth embodiment. Configurations of the container 10 and the terahertz wave measurement device according to the eighth embodiment are approximately the same as those according to the first embodiment. It should be noted that the DUT 1 is cylindrical, and an entirety of the DUT 1 is stored in the gap portion 11 (or the through gap portion 110) of the container 10.

It should be noted that the bolt head portions 14a, the nuts 14b, the bolt thread portions 14c, the upper pressing member 16a, and the lower pressing member 16b according to the first embodiment are not shown in FIGS. 15(a) and 15(b). The bolt head portions 14a, the nuts 14b, and the bolt thread portions 14c according to the second embodiment are not shown. The bolt head portions 14a, the nuts 14b, the bolt thread portions 14c, the upper pressing member 16a, and the lower pressing member 16b according to the third embodiment are not shown. When the container 10 according to the second and third embodiments is used to scan the DUT 1, the enclosure portion 12 in FIGS. 15(a) and 15(b) schematically shows the shape of the container 10 (simply shows a rough contour of the container 10, and does not show the respective first structures 100 and the like).

A description will now be given of an operation of the eighth embodiment. It should be noted that the definitions of the output step, the detection step, and the definitions of the optical paths P1 and P2 are the same as those of the fourth embodiment.

Referring to FIG. 15(a), the output step is carried out. The output terahertz wave transmits through the enclosure portion 12 and the DUT 1 while traveling straight as described in the first embodiment. Then, the detection step is carried out. As a result, a lower part of the DUT 1 is measured by the terahertz wave measurement device.

During the output step and the detection step, the container 10 and the DUT 1 move vertically (downward in FIGS. 15(a) and 15(b)) with respect to the optical paths P1 and P2 of the terahertz wave. Then, the optical path P2 intersects with an upper part of the DUT 1 as shown in FIG. 15(b). As a result, the upper part of the DUT 1 is measured by the terahertz wave measurement device.

According to the eighth embodiment, the DUT 1 can be scanned in the vertical direction (Z direction). As a result, the DUT 1 can be tomographically measured.

During the output step and the detection step, the optical paths P1 and P2 of the terahertz wave may move vertically with respect to the container 10 and the DUT 1.

Ninth Embodiment

A ninth embodiment is different from the first to third embodiments in that arrangement of the container 10 according to the first to third embodiments with respect to the terahertz wave measurement device.

Figure 16:
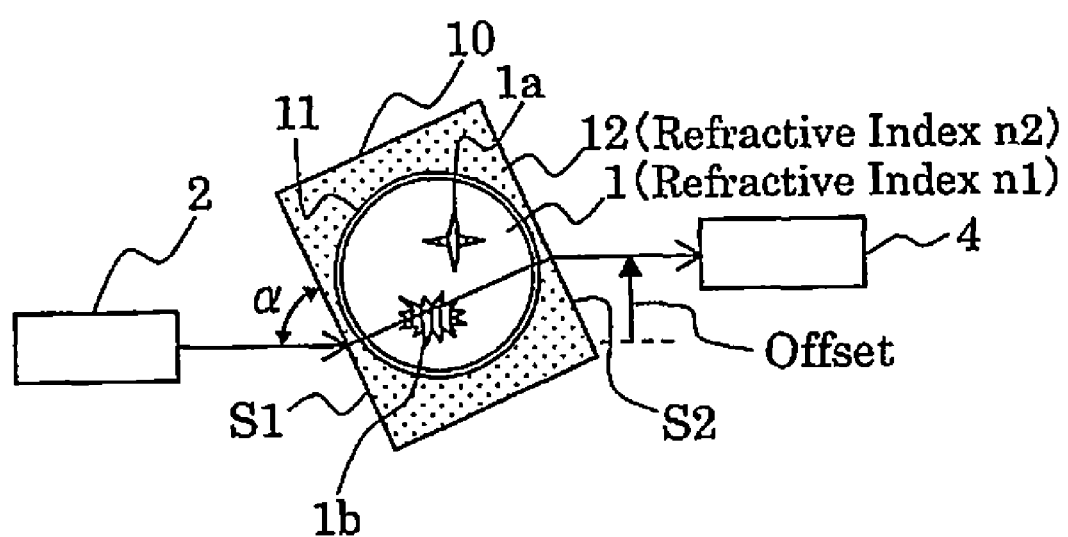
FIG. 16 is a plan view of a state in which at least a part of the DUT 1 is stored in the container 10 according to the ninth embodiment, and the terahertz wave is irradiated on the container 10.

FIG. 16 is a plan view of a state in which at least a part of the DUT 1 is stored in the container 10 according to the ninth embodiment, and the terahertz wave is irradiated on the container 10. Components omitted in FIG. 16 are the same as those of the fourth embodiment. Moreover, when the DUT 1 is scanned using the container 10 according to the second and third embodiments, the container 10 in FIG. 16 is the first structure 100 as in the fourth embodiment.

Configurations of the container 10 and the terahertz wave measurement device are similar to those of the first to third embodiments, and a description thereof, therefore, is omitted.

It should be noted that, referring to FIG. 16, the first flat surface portion S1 intersects with the travel direction of the terahertz wave output from the terahertz wave output device 2 of the terahertz wave measurement device toward the DUT 1 at an angle α, which is more than 0 degree and less than 90 degrees. The container 10 is provided as described above so as to measure the DUT 1 by the terahertz wave measurement device. This implies that the direction of the normal line of the first flat surface portion S1 intersects with the travel direction of the terahertz wave output from the terahertz wave output device 2 of the terahertz wave measurement device toward the DUT 1 at an angle (=90 degrees−α), which is more than 0 degree and less than 90 degrees.

When this method is applied to the variation of the second embodiment (refer to FIG. 8) and the variation of the third embodiment (refer to FIG. 10), the predetermined direction (Y direction) is set so as to intersect with the travel direction of the terahertz wave output from the terahertz wave output device 2 of the terahertz wave measurement device toward the DUT 1 at an angle more than 0 degree and less than 90 degrees.

A description will now be given of an operation of the ninth embodiment.

Referring to FIG. 16, the terahertz wave output device 2 of the terahertz wave measurement device outputs the terahertz wave. The terahertz wave output from the terahertz wave output device 2 is irradiated on the first flat surface portion S1. On this occasion, the terahertz wave is refracted, and then travels straight inside the enclosure portion 12.

On this occasion, the thickness of the air layer between the contour of the DUT 1 and the contour of the plane shape of the gap portion 11 is thin, and is thus neglected. Further, it is assumed that the refractive index n2 has been adjusted such that the relationship (refractive index n1 of DUT 1)=(refractive index n2 of the enclosure portion 12) holds.

The terahertz wave, which has traveled inside the enclosure portion 12, is not refracted, but travels straight inside the DUT 1. Further, the terahertz wave transmits through the DUT 1, and is made incident to the enclosure portion 12. Then, the terahertz wave travels straight inside the enclosure portion 12, and transmits through the second flat surface portion S2. On this occasion, the terahertz wave is refracted, travels in a direction parallel with the travel direction of the terahertz wave output from the terahertz wave output device 2, and is made incident to the terahertz wave detector 4.

Eventually, the optical path of the terahertz wave output from the terahertz wave output device 2 is displaced by a predetermined distance (offset), and the terahertz wave is made incident to the terahertz wave detector 4.

The terahertz wave detector 4 detects the incident terahertz wave. As a result, the DUT 1 is measured. For example, the DUT 1 includes contents 1a and 1b. Referring to FIG. 16, the terahertz wave transmits through the content 1b, and thus, the position and the like of the content 1b are revealed according to a result of the detection of the terahertz wave.

Though the operation of the ninth embodiment is described while assuming that the relationship (refractive index n1 of DUT 1)=(refractive index n2 of enclosure portion 12) holds, an approximately similar operation is provided when the relationship n1−0.1≦n2≦n1+0.1 holds.

According to the ninth embodiment, it is possible to restrain the terahertz wave from being refracted by the DUT 1 when the DUT 1 is measured by supplying the DUT 1 with the terahertz wave.

Moreover, according to the ninth embodiment, the optical path of the terahertz wave output from the terahertz wave output device 2 is displaced by the predetermined distance (offset), and the terahertz wave is made incident to the terahertz wave detector 4. As a result, the ninth embodiment is suitable for a case in which the terahertz wave detector 4 is not present in the travel direction of the terahertz wave output from the terahertz wave output device 2.

Tenth Embodiment

The tenth embodiment is different from the first embodiment in that enclosure portions 12a and 12b can be separated along separation surfaces D1 and D2. It should be noted that the container 10 according to the tenth embodiment can be used to scan the DUT 1 described in the fourth to eighth embodiments. Moreover, as an arrangement of the container 10 according to the tenth embodiment, the method described in the ninth embodiment (refer to FIG. 16) may be employed.

Figure 17:
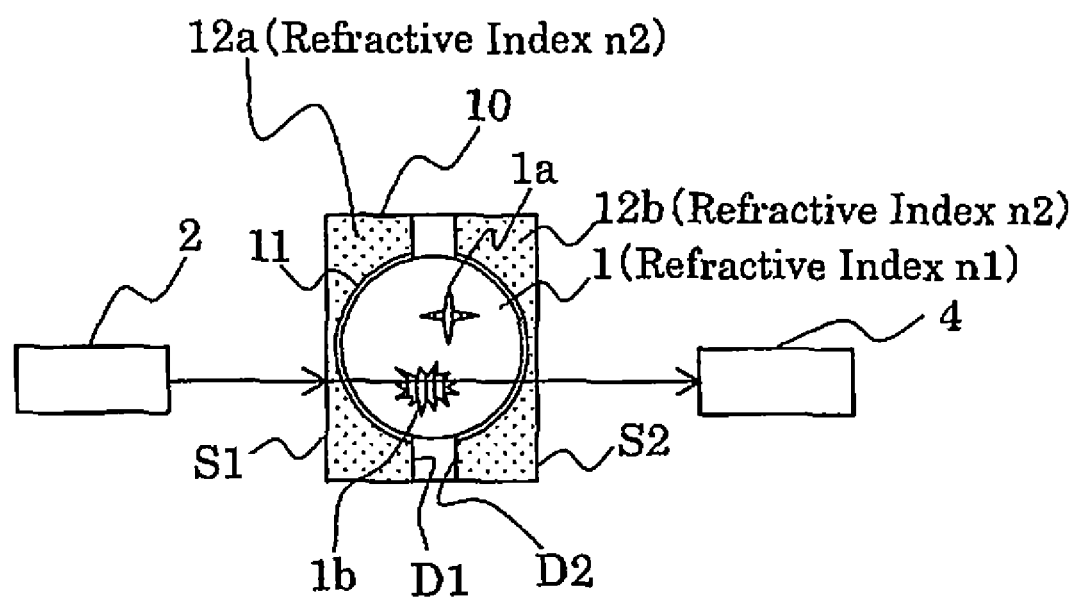
FIG. 17 is a plan view of a state in which at least a part of the DUT 1 is stored in the container 10 according to the tenth embodiment, and the terahertz wave is irradiated on the container 10.

FIG. 17 is a plan view of a state in which at least a part of the DUT 1 is stored in the container 10 according to the tenth embodiment, and the terahertz wave is irradiated on the container 10.

The configurations of the container 10 and the terahertz wave measurement device are approximately the same as those of the first embodiment. It should be noted that the container 10 includes the enclosure portions 12a and 12b in place of the enclosure portion 12. The enclosure portions 12a and 12b can be separated along the separation surfaces D1 and D2. Moreover, the separation surfaces D1 and D2 intersect with the gap portion 11. It should be noted that the partition surfaces D1 and D2 may be separated from each other as shown in FIG. 17. Moreover, the enclosure portions 12a and 12b are coupled to each other by coupling Means, which is not shown. In the case shown in FIG. 17, the contour of a plane shape of the gap portion 11 includes an arc protruding leftward and an arc protruding rightward.

An operation of the tenth embodiment is the same as the operation of the first embodiment, and hence a description thereof is omitted.

With the container 10 according to the tenth embodiment, since the enclosure portions 12a and 12b can be separated along the separation surfaces D1 and D2, the DUT 1 can be easily stored in the gap portion 11. For example, the enclosure portions 12a and 12b are separated along the separation surfaces D1 and D2, and the DUT 1 is then stored inside the gap portion 11. Then, the enclosure portions 12a and 12b may be coupled to each other by the coupling means, which is not shown.

It should be noted that the containers 10 according to the second and third embodiments (FIGS. 7(a), 7(b), 7(c), 8, 9(a), 9(b), 9(c), and 10) may be separated along the separation surfaces as described above. In other words, the first enclosure portion 12' in FIGS. 7(a), 7(b), and 7(c), the container 10 in FIG. 8 (separable in the Y direction, for example), the first enclosure portion 12' and the second enclosure portion 132 in FIGS. 9(a), 9(b), and 9(c), and the container 10 in FIG. 10 (separable in the Y direction, for example) may be configured as separable.

Eleventh Embodiment

The container 10 according to the eleventh embodiment is adapted to a case in which the DUT 1 is constructed by multiple cylinders. It should be noted that the container 10 according to the eleventh embodiment can be used to scan the DUT 1 described in the fourth to eighth embodiments. Moreover, as an arrangement of the container 10 according to the eleventh embodiment, the method described in the ninth embodiment (refer to FIG. 16) may be employed.

Figure 18:
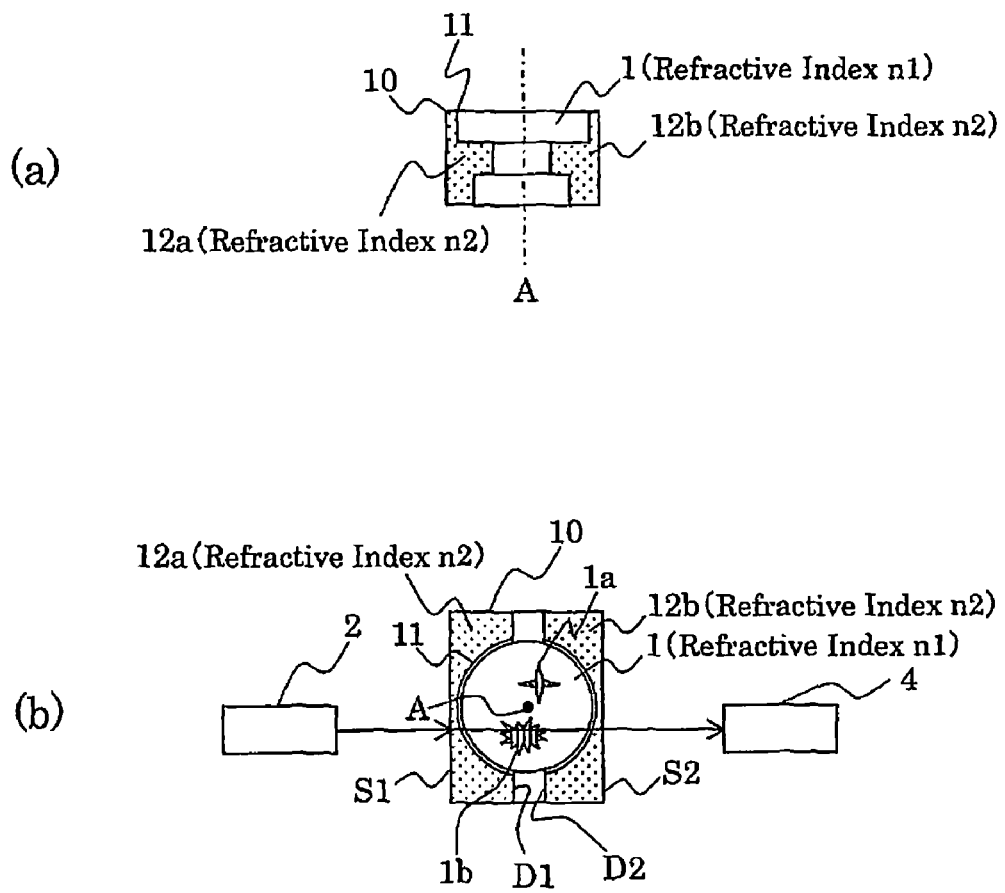

FIGS. 18(a) and 18(b) are views when the DUT 1 is stored in the container 10 according to the eleventh embodiment, in which FIG. 18(a) is a cross sectional view, and FIG. 18(b) is a plan view. It should be noted that the gap between the container 10 and the gap portion 11 is omitted for the sake of illustration in FIG. 18(a).

Referring to FIG. 18(a), the DUT 1 is constructed by three cylinders, and the diameter of a bottom surface changes according to the height ([diameter of bottom surface of top cylinder]>[diameter of bottom surface of bottom cylinder]>[diameter of bottom surface of middle cylinder]). It is only necessary for the DUT 1 to form a solid revolution, and may be an ellipsoid, for example. It should be noted that the center axis of the solid revolution needs to coincide with the line A.

On this occasion, a radius of a contour of a plane shape of the gap portion 11 changes according to the height of the gap portion 11. This corresponds to the case that the diameter of the bottom surface of the DUT 1 changes according to the height thereof.

Referring to FIG. 18(b), the enclosure portions 12a and 12b can be separated along the separation surfaces D1 and D2. Moreover, the separation surfaces D1 and D2 intersect with the gap portion 11 (which is the same as the tenth embodiment). As a result, the DUT 1 can be easily stored in the gap portion 11. For example, the enclosure portions 12a and 12b are separated along the separation surfaces D1 and D2, and the DUT 1 is then stored inside the gap portion 11. Then, the enclosure portions 12a and 12b may be coupled to each other by the coupling means, which is not shown.

It should be noted that the positions of the terahertz wave output device 2 and the terahertz wave detector 4 of the terahertz wave measurement device and the positions of the optical paths P1 and P2 in FIG. 18(b) are similar to those in FIGS. 11(a) and 11(b), and hence a description thereof is omitted.

It should be noted that a radius of a contour of a plane shape of the first gap portions 11' of the container 10 according to the second embodiment (refer to FIGS. 7(a), 7(b), and 7(c)) may change according to the height of the first gap portions 11'.

It should be noted that a radius of a contour of a plane shape of the through gap portions 110 of the container 10 according to the variation of the second embodiment (refer to FIG. 8) may change according to the height of the through gap portions 110.

It should be noted that a radius of a contour of a plane shape of the first gap portions 11' and the second gap portions 131 of the container 10 according to the third embodiment (refer to FIGS. 9(a), 9(b), and 9(c)) may change according to the height of the first gap portions 11' and the second gap portions 131.

It should be noted that a radius of a contour of a plane shape of the through gap portions 110 of the container 10 according to the variation of the third embodiment (refer to FIG. 10) may change according to the height of the through gap portions 110.

The invention claimed is:

1. A container that contains at least a part of a device under test to be measured by an electromagnetic wave measurement device, comprising:
    a gap portion that internally receives at least a part of the device under test; and
    an enclosure portion that comprises a first flat surface portion and a second flat surface portion, and the gap portion is positioned between the first flat surface portion and the second flat surface portion, whereby the enclosure portion encloses the gap portion, wherein:
    n2 can be adjusted such that:

$$n1-0.1 \leq n2 \leq n1+0.1$$

where n2 denotes a refractive index of the enclosure portion and n1 denotes a refractive index of the device under test; and
        the electromagnetic wave measurement device outputs an electromagnetic wave having a frequency equal to or more than 0.01 THz and equal to or less than 100 THz toward the device under test,
        wherein the refractive index of the enclosure portion can be adjusted by changing a thickness of the enclosure portion.

2. The container according to claim 1, wherein the refractive index of the enclosure portion can be changed by compressing or extending the enclosure portion.

3. The container according to claim 2, wherein the enclosure portion comprises a foamable resin.

4. The container according to claim 2, wherein:
    the device under test receives the electromagnetic wave while the device under test is rotated about a predetermined rotational axis; and
    the enclosure portion is compressed or extended in a direction of the predetermined rotational axis.

5. The container according to claim 2, wherein:
    the device under test receives the electromagnetic wave while the device under test is rotated about a predetermined rotational axis; and
    the enclosure portion is compressed or extended in a direction orthogonal to the predetermined rotational axis, and to an optical path of the electromagnetic wave.

6. The container according to claim 2, wherein:
    the device under test receives the electromagnetic wave while the container and an optical path of the electromagnetic wave are rotated about a predetermined rotational axis; and
    the enclosure portion is compressed or extended in the direction of the predetermined rotational axis.

7. The container according to claim 2, wherein:
    the device under test receives the electromagnetic wave while the container and an optical path of the electromagnetic wave are rotated about a predetermined rotational axis; and
    the enclosure portion is compressed or extended in a direction orthogonal to the predetermined rotational axis, and to the optical path of the electromagnetic wave.

8. The container according to claim 2, wherein the enclosure portion is compressed or extended in a direction parallel with an optical path of the electromagnetic wave.

9. The container according to claim 1, wherein a contour of a plane shape of the gap portion includes an arc.

10. The container according to claim 9, wherein a radius of the contour of the plane shape of the gap portion changes according to the height of the gap portion.

11. The container according to claim 1, wherein:
    the enclosure portion can be separated along a separation surface; and
    the separation surface intersects with the gap portion.

12. A refractive index adjustment method for adjusting the refractive index of the enclosure portion of the container according to claim 1 containing the device under test comprising:
    arranging the container such that the first flat surface portion intersects with a travel direction of the electromagnetic wave output from the electromagnetic wave measurement device toward the device under test at a right angle; and
    adjusting the refractive index of the enclosure portion such that an optical path of the electromagnetic wave incident to the first flat surface portion and an optical path of the electromagnetic wave which has transmitted through the enclosure portion and the device under test are aligned along a straight line.

13. A container arrangement method for arranging the container according to claim 1 containing the device under test for measuring the device under test by the electromagnetic wave measurement device, comprising arranging the container such that the first flat surface portion intersects with a travel direction of the electromagnetic wave output from the electromagnetic wave measurement device toward the device under test at a right angle.

14. A container arrangement method for arranging the container according to claim 1 containing the device under test for measuring the device under test by the electromagnetic wave measurement device, comprising arranging the container such that the first flat surface portion intersects with a travel direction of the electromagnetic wave output from the electromagnetic wave measurement device toward the device under test at an angle more than 0 degree and less than 90 degrees.

15. A method for measuring the device under test contained in the container according to claim 1 using the electromagnetic wave measurement device, comprising:
    outputting the electromagnetic wave by the electromagnetic wave measurement device; and
    detecting the electromagnetic wave which has transmitted through the device under test by the electromagnetic wave measurement device,
    wherein the container and the device under test move horizontally with respect to an optical path of the electromagnetic wave while the outputting and the detecting are being carried out.

16. A method for measuring the device under test contained in the container according to claim 1 using the electromagnetic wave measurement device, comprising:
    outputting the electromagnetic wave by the electromagnetic wave measurement device; and
    detecting the electromagnetic wave which has transmitted through the device under test by the electromagnetic wave measurement device,
    wherein an optical path of the electromagnetic wave move moves horizontally with respect to the container while the outputting and the detecting are being carried out.

17. A method for measuring the device under test contained in the container according to claim 1 using the electromagnetic wave measurement device, comprising:
    outputting the electromagnetic wave by the electromagnetic wave measurement device; and
    detecting the electromagnetic wave which has transmitted through the device under test by the electromagnetic wave measurement device, wherein the device under test is rotated about a line extending vertically as a rotational axis while the outputting and the detecting are being carried out.

18. A method for measuring the device under test contained in the container according to claim 1 using the electromagnetic wave measurement device, comprising:
outputting the electromagnetic wave by the electromagnetic wave measurement device; and
detecting the electromagnetic wave which has transmitted through the device under test by the electromagnetic wave measurement device,
wherein the container and an optical path of the electromagnetic wave are rotated about a line extending vertically as a rotational axis while the outputting and the detecting are being carried out.

19. A method for measuring the device under test contained in the container according to claim 1 using the electromagnetic wave measurement device, comprising:
outputting the electromagnetic wave by the electromagnetic wave measurement device; and
detecting the electromagnetic wave which has transmitted through the device under test by the electromagnetic wave measurement device,
wherein the container and an optical path of the electromagnetic wave move vertically with respect to the device under test while the outputting and the detecting are being carried out.

20. A method for measuring the device under test contained in the container according to claim 1 using the electromagnetic wave measurement device, comprising:
outputting the electromagnetic wave by the electromagnetic wave measurement device; and
detecting the electromagnetic wave which has transmitted through the device under test by the electromagnetic wave measurement device,
wherein the container and the device under test move vertically with respect to an optical path of the electromagnetic wave while the outputting and the detecting are being carried out.

21. A method for measuring the device under test contained in the container according to claim 1 using the electromagnetic wave measurement device, comprising:
outputting the electromagnetic wave by the electromagnetic wave measurement device; and
detecting the electromagnetic wave which has transmitted through the device under test by the electromagnetic wave measurement device,
wherein the device under test moves vertically with respect to the container and an optical path of the electromagnetic wave while the outputting and the detecting are being carried out.

22. A method for measuring the device under test contained in the container according to claim 1 using the electromagnetic wave measurement device, comprising:
outputting the electromagnetic wave by the electromagnetic wave measurement device; and
detecting the electromagnetic wave which has transmitted through the device under test by the electromagnetic wave measurement device,
wherein an optical path of the electromagnetic wave moves vertically with respect to the container and the device under test while the outputting and the detecting are being carried out.

23. A container that contains at least a part of a device under test to be measured by an electromagnetic wave measurement device, comprising a plurality of first structures that comprise:
a first gap portion which internally receives at least a part of the device under test, and
a first enclosure portion which includes a first flat surface portion and a second flat surface portion, and the first gap portion is positioned between the first flat surface portion and the second flat surface portion, whereby the first enclosure portion encloses the first gap portion, wherein:
the first structures are separated by a predetermined interval;
n2 can be adjusted such that:
n1−0.1≦n2≦n1+0.1
where n2 denotes an average refractive index of the container and n1 denotes a refractive index of the device under test; and
the electromagnetic wave measurement device outputs an electromagnetic wave having a frequency equal to or more than 0.01 THz and equal to or less than 100 THz toward the device under test.

24. The container according to claim 23, wherein the average refractive index of the container can be changed by changing the predetermined interval.

25. The container according to claim 24, wherein the predetermined interval is changed by compressing or extending the container.

26. The container according to claim 25, wherein:
the device under test receives the electromagnetic wave while rotating about a predetermined rotational axis; and
the container is compressed or extended in the direction of the predetermined rotational axis.

27. The container according to claim 25, wherein:
the device under test receives the electromagnetic wave while the container and an optical path of the electromagnetic wave are rotated about a predetermined rotational axis; and
the container is compressed or extended in the direction of the predetermined rotational axis.

28. The container according to claim 23, comprising an interval retaining member that is provided between a plurality of the first structures, and is provided outside the first gap portion.

29. The container according to claim 23, comprising a second structure provided between a plurality of the first structures, wherein the second structure comprises:
a second gap portion which internally receives at least a part of the device under test; and
a second enclosure portion which includes a third flat surface portion and a fourth flat surface portion, and the second gap portion is positioned between the third flat surface portion and the fourth flat surface portion, whereby the second enclosure portion encloses the second gap portion.

30. The container according to claim 23, wherein the predetermined interval is determined so as not to cause a Bragg reflection of the electromagnetic wave.

31. The container according to claim 23, wherein the predetermined intervals are equal to each other.

32. The container according to claim 23, wherein the predetermined intervals include an unequal interval.

33. The container according to claim 23, wherein a contour of a plane shape of the first gap portion includes an arc.

34. The container according to claim 33, wherein a radius of the contour of the plane shape of the first gap portion changes according to the height of the first gap portion.

35. The container according to claim 23, wherein:
the first enclosure portion can be separated along a separation surface; and
the separation surface intersects with the first gap portion.

36. A refractive index adjustment method for adjusting the average refractive index of the container according to claim 23 containing the device under test, comprising:
arranging the container so that a normal direction of the first flat surface portion is parallel with a travel direction of the electromagnetic wave output from the electromagnetic wave measurement device toward the device under test; and
adjusting the average refractive index of the container such that an optical path of the electromagnetic wave incident to the first flat surface portion and an optical path of the electromagnetic wave which has transmitted through the container and the device under test are aligned on a straight line.

37. A container arrangement method for arranging the container according to claim 23 containing the device under test for measuring the device under test by the electromagnetic wave measurement device, comprising arranging the container so that a normal direction of the first flat surface portion is parallel with a travel direction of the electromagnetic wave output from the electromagnetic wave measurement device toward the device under test.

38. A container arrangement method for arranging the container according to claim 23 containing the device under test for measuring the device under test by the electromagnetic wave measurement device, comprising arranging the container such that a normal direction of the first flat surface portion intersects with a travel direction of the electromagnetic wave output from the electromagnetic wave measurement device toward the device under test at an angle more than 0 degree and less than 90 degrees.

39. A container that contains at least a part of a device under test to be measured by an electromagnetic wave measurement device, comprising a plurality of first structures that are separated by a predetermined interval in a predetermined direction, wherein:
n2 can be adjusted such that:

$$n1-0.1 \leq n2 \leq n1+0.1$$

where n2 denotes an average refractive index of the container and n1 denotes a refractive index of the device under test;
the electromagnetic wave measurement device outputs an electromagnetic wave having a frequency equal to or more than 0.01 THz and equal to or less than 100 THz toward the device under test;
a through gap portion which passes through the container and internally receives at least a part of the device under test; and
an extending direction of the through gap portion and the predetermined direction intersects with each other at a right angle.

40. The container according to claim 39, wherein the average refractive index of the container can be changed by changing the predetermined interval.

41. The container according to claim 40, wherein the predetermined interval is changed by compressing or extending the container.

42. The container according to claim 39, comprising an interval retaining member that is provided between a plurality of the first structures.

43. The container according to claim 39, comprising a second structure provided between a plurality of the first structures.

44. The container according to claim 39, wherein the predetermined interval is determined so as not to cause a Bragg reflection of the electromagnetic wave.

45. The container according to claim 39, wherein the predetermined intervals are equal to each other.

46. The container according to claim 39, wherein the predetermined intervals include an unequal interval.

47. The container according to claim 39, wherein:
the device under test receives the electromagnetic wave while the device under test is rotated about a predetermined rotational axis; and
the container is compressed or extended in a direction orthogonal to the predetermined rotational axis, and to an optical path of the electromagnetic wave.

48. The container according to claim 39, wherein:
the device under test receives the electromagnetic wave while the container and an optical path of the electromagnetic wave are rotated about a predetermined rotational axis; and
the container is compressed or extended in a direction orthogonal to the predetermined rotational axis, and to an optical path of the electromagnetic wave.

49. The container according to claim 39, wherein the container is compressed or extended in a direction parallel with an optical path of the electromagnetic wave.

50. The container according to claim 39, wherein a contour of a plane shape of the through gap portion includes an arc.

51. The container according to claim 50, wherein a radius of the contour of the plane shape of the through gap portion changes according to the height of the through gap portion.

52. The container according to claim 39, wherein: the container can be separated along a separation surface; and the separation surface intersects with the through gap portion.

53. A refractive index adjustment method for adjusting the average refractive index of the container according to claim 39 containing the device under test, comprising:
arranging the container so that the predetermined direction is parallel with or orthogonal to a travel direction of the electromagnetic wave output from the electromagnetic wave measurement device toward the device under test; and
adjusting the average refractive index of the container such that an optical path of the electromagnetic wave incident to the container and an optical path of the electromagnetic wave which has transmitted through the container and the device under test are aligned on a straight line.

54. A container arrangement method for arranging the container according to claim 39 containing the device under test for measuring the device under test by the electromagnetic wave measurement device, comprising arranging the container such that the predetermined direction is parallel with or orthogonal to a travel direction of the electromagnetic wave output from the electromagnetic wave measurement device toward the device under test.

55. A container arrangement method for arranging the container according to claim 39 containing the device under test for measuring the device under test by the electromagnetic wave measurement device, comprising arranging the container such that the predetermined direction intersects with a travel direction of the electromagnetic wave output from the electromagnetic wave measurement device toward the device under test at an angle more than 0 degree and less than 90 degrees.

* * * * *